(12) United States Patent
Jahani et al.

(10) Patent No.: US 12,059,371 B2
(45) Date of Patent: Aug. 13, 2024

(54) OCULAR REGION HEAT TRANSFER DEVICES AND ASSOCIATED SYSTEMS AND METHODS

(71) Applicant: BlueXthermal, Inc., Cambridge, MA (US)

(72) Inventors: Sahar Jahani, Boston, MA (US); Reza Monazami, Boston, MA (US); Nicholas Keith Anselmo, Yorktown, VA (US)

(73) Assignee: BLUEXTHERMAL, INC., Cambridge, MA (US)

( * ) Notice: Subject to any disclaimer, the term of this patent is extended or adjusted under 35 U.S.C. 154(b) by 0 days.

(21) Appl. No.: 18/149,574

(22) Filed: Jan. 3, 2023

(65) Prior Publication Data
US 2023/0263656 A1    Aug. 24, 2023

Related U.S. Application Data

(60) Provisional application No. 63/266,400, filed on Jan. 4, 2022.

(51) Int. Cl.
| | |
|---|---|
| *A61F 7/00* | (2006.01) |
| *G01K 7/42* | (2006.01) |
| *H10N 10/13* | (2023.01) |

(52) U.S. Cl.
CPC ............ *A61F 7/007* (2013.01); *A61F 7/0085* (2013.01); *G01K 7/425* (2013.01); *H10N 10/13* (2023.02);
(Continued)

(58) Field of Classification Search
CPC ...... A61F 2007/0004; A61F 2007/0054; A61F 2007/0055; A61F 2007/0056;
(Continued)

(56) References Cited

U.S. PATENT DOCUMENTS

| | | |
|---|---|---|
| 4,351,388 A | 9/1982 | Calhoun et al. |
| 4,423,718 A | 1/1984 | Garrison |
| (Continued) | | |

FOREIGN PATENT DOCUMENTS

| | | |
|---|---|---|
| CA | 2275387 | 4/1999 |
| CN | 103356279 | 10/2013 |
| (Continued) | | |

OTHER PUBLICATIONS

Wang, Hao, "An analytical solution for the total heat transfer in the thin-film region of an evaporating meniscus", International Journal of Heat and Mass Transfer, 51, 25-26, (2008), 6317-6322.
(Continued)

*Primary Examiner* — Kaitlyn E Smith
*Assistant Examiner* — Bradford C. Blaise
(74) *Attorney, Agent, or Firm* — Perkins Coie LLP

(57) ABSTRACT

Wearable heat transfer devices and associated systems and methods are disclosed herein. In some embodiments, a representative heat transfer device can comprise (i) a thermoelectric component (TEC) including a first side configured to be operated at a desired temperature and a second side opposite the first side, (ii) a thermally conductive contact member thermally coupled to the TEC, and (iii) a heat transfer system configured to distribute heat from the TEC. The heat transfer system includes a heat transfer structure thermally coupled to the TEC, and a heat exchanger thermally coupled to the heat transfer structure.

30 Claims, 27 Drawing Sheets

(52) U.S. Cl.
CPC .............. *A61F 2007/0004* (2013.01); *A61F 2007/0075* (2013.01)

(58) Field of Classification Search
CPC ...... A61F 2007/0057; A61F 2007/0058; A61F 2007/0075; A61F 7/007; A61F 7/0085; H10N 10/13; G01K 7/425
See application file for complete search history.

(56) References Cited

U.S. PATENT DOCUMENTS

| | | | |
|---|---|---|---|
| 5,411,077 | A | 5/1995 | Tousignant |
| 5,453,641 | A | 9/1995 | Mundinger et al. |
| 5,737,923 | A | 4/1998 | Gilley et al. |
| 5,986,884 | A | 11/1999 | Jairazbhoy et al. |
| 6,062,210 | A | 5/2000 | Welles |
| 6,140,707 | A | 10/2000 | Plepys et al. |
| 6,233,944 | B1 | 5/2001 | Yamada et al. |
| 6,253,838 | B1 | 7/2001 | Fiechter et al. |
| 6,338,251 | B1 | 1/2002 | Ghoshal |
| 6,418,017 | B1 | 7/2002 | Patel et al. |
| 6,474,074 | B2 | 11/2002 | Ghoshal |
| 6,483,705 | B2 | 11/2002 | Snyder et al. |
| 6,489,551 | B2 | 12/2002 | Chu |
| 6,770,085 | B1* | 8/2004 | Munson ............ A61F 7/02 607/104 |
| 6,840,310 | B2 | 1/2005 | Tonosaki et al. |
| 6,845,622 | B2 | 1/2005 | Sauciuc |
| 6,934,154 | B2 | 8/2005 | Prasher et al. |
| 6,988,382 | B2 | 1/2006 | Upadhya |
| 6,988,534 | B2 | 1/2006 | Kenny |
| 7,000,684 | B2 | 2/2006 | Kenny |
| 7,032,389 | B2 | 4/2006 | Cauchy |
| 7,059,396 | B2 | 6/2006 | Foli |
| 7,123,479 | B2 | 10/2006 | Chang et al. |
| 7,278,269 | B2 | 10/2007 | Pham |
| 7,342,787 | B1 | 3/2008 | Bhatia |
| 7,369,410 | B2 | 5/2008 | Chen et al. |
| 7,571,618 | B2 | 8/2009 | Dessiatoun |
| 7,645,263 | B2 | 1/2010 | Angel et al. |
| 7,665,511 | B2 | 2/2010 | Bhatti et al. |
| 7,791,885 | B2 | 9/2010 | Agostini et al. |
| 7,856,831 | B2 | 12/2010 | Flinner |
| 7,926,293 | B2 | 4/2011 | Bell |
| 7,957,137 | B2 | 6/2011 | Prasher |
| 7,992,626 | B1 | 8/2011 | Tilton et al. |
| 8,056,347 | B2 | 11/2011 | Flinner |
| 8,058,724 | B2 | 11/2011 | Refai-Ahmed |
| 8,081,465 | B2 | 12/2011 | Nishiura |
| 8,165,702 | B2 | 4/2012 | Wyatt et al. |
| 8,255,193 | B2 | 8/2012 | Humphrey et al. |
| 8,360,361 | B2 | 1/2013 | Wadley et al. |
| 8,464,781 | B2 | 6/2013 | Kenny |
| 8,474,446 | B1 | 7/2013 | Rohr et al. |
| 8,593,810 | B2 | 11/2013 | Yoshikawa et al. |
| 8,621,875 | B2 | 1/2014 | Parish et al. |
| 8,987,893 | B1 | 3/2015 | Sutardja et al. |
| 9,301,433 | B2 | 3/2016 | Campbell |
| 9,435,553 | B2 | 9/2016 | Quisenberry |
| 9,468,488 | B2 | 10/2016 | Bates et al. |
| 9,504,189 | B1 | 11/2016 | Campbell et al. |
| 9,857,107 | B2 | 1/2018 | Inaba |
| 10,217,692 | B2 | 2/2019 | Haj-Hariri et al. |
| 10,760,827 | B2 | 9/2020 | Quisenberry |
| 11,213,422 | B1 | 1/2022 | Monazami et al. |
| 11,766,352 | B2 | 9/2023 | Monazami |
| 11,768,016 | B2 | 9/2023 | Monazami et al. |
| 2002/0062648 | A1 | 5/2002 | Ghoshal |
| 2002/0062855 | A1 | 5/2002 | Chu |
| 2002/0135980 | A1 | 9/2002 | Vafai |
| 2003/0037907 | A1 | 2/2003 | Lee |
| 2003/0089486 | A1 | 5/2003 | Parish et al. |
| 2004/0238022 | A1 | 12/2004 | Hiller |
| 2005/0028858 | A1 | 2/2005 | Rossi |
| 2005/0081552 | A1 | 4/2005 | Nilson et al. |
| 2005/0085018 | A1 | 4/2005 | Kim et al. |
| 2006/0053805 | A1 | 3/2006 | Flinner |
| 2006/0075761 | A1 | 4/2006 | Kitchens |
| 2006/0090787 | A1 | 5/2006 | Onvural |
| 2007/0034356 | A1 | 2/2007 | Kenny et al. |
| 2007/0039720 | A1 | 2/2007 | Ghosh et al. |
| 2007/0167776 | A1 | 7/2007 | Kochavi et al. |
| 2007/0240856 | A1 | 10/2007 | Liu et al. |
| 2008/0128109 | A1 | 6/2008 | Gwin et al. |
| 2008/0170368 | A1 | 7/2008 | Chen et al. |
| 2008/0188915 | A1* | 8/2008 | Mills .............. A61F 7/007 607/112 |
| 2008/0229759 | A1 | 9/2008 | Ouyang et al. |
| 2008/0295996 | A1 | 12/2008 | Bhavnani et al. |
| 2009/0140417 | A1 | 6/2009 | Refai-Ahmed |
| 2010/0018221 | A1 | 1/2010 | Flinner |
| 2010/0314088 | A1 | 12/2010 | Yoo et al. |
| 2011/0023927 | A1 | 2/2011 | Hsu et al. |
| 2011/0075372 | A1 | 3/2011 | Zimbeck et al. |
| 2011/0106071 | A1 | 5/2011 | Bosel |
| 2012/0111028 | A1 | 5/2012 | Campbell et al. |
| 2012/0290023 | A1 | 11/2012 | Boyden et al. |
| 2013/0014916 | A1 | 1/2013 | Wadley et al. |
| 2013/0281893 | A1* | 10/2013 | Yang .............. A61H 1/00 607/109 |
| 2013/0331914 | A1* | 12/2013 | Lee .............. A61F 7/007 607/96 |
| 2014/0026637 | A1 | 1/2014 | Blanc et al. |
| 2014/0334106 | A1 | 11/2014 | Prest et al. |
| 2015/0060023 | A1 | 3/2015 | Herring et al. |
| 2015/0083180 | A1 | 3/2015 | Lang |
| 2015/0198380 | A1 | 7/2015 | Haj-Hariri et al. |
| 2015/0238349 | A1 | 8/2015 | Giuliani |
| 2016/0000600 | A1* | 1/2016 | Lee .............. A61F 7/00 607/109 |
| 2016/0035957 | A1 | 2/2016 | Casey |
| 2016/0270951 | A1* | 9/2016 | Martins .............. A61B 18/02 |
| 2018/0147086 | A1 | 5/2018 | Evans et al. |
| 2020/0155342 | A1 | 5/2020 | Schultz |
| 2020/0206023 | A1* | 7/2020 | Pathak .............. A61F 7/00 |
| 2020/0368062 | A1 | 11/2020 | Baker et al. |
| 2021/0030141 | A1 | 2/2021 | Goo |
| 2021/0085518 | A1 | 3/2021 | Lessing et al. |
| 2021/0123641 | A1 | 4/2021 | Monazami et al. |
| 2022/0265467 | A1 | 8/2022 | Monazami et al. |
| 2022/0273088 | A1 | 9/2022 | Goo |
| 2022/0273088 | A1* | 9/2022 | Goo .............. A45D 44/002 |

FOREIGN PATENT DOCUMENTS

| | | |
|---|---|---|
| CN | 103431906 | 12/2013 |
| CN | 109260596 | 1/2019 |
| DE | 102007050391 | 4/2008 |
| EP | 281405 | 9/1988 |
| JP | H11121816 | 4/1999 |
| JP | 2001077566 | 3/2001 |
| WO | 2002065029 | 8/2002 |
| WO | 2007139814 | 12/2007 |
| WO | 2011142841 | 11/2011 |
| WO | 2013085552 | 6/2013 |
| WO | 2014001789 | 1/2014 |
| WO | 2014057450 | 4/2014 |
| WO | 2014143305 | 9/2014 |
| WO | 2016014710 | 1/2016 |
| WO | 2018165086 | 9/2018 |
| WO | 2018225913 | 12/2018 |
| WO | 2021016399 | 1/2021 |
| WO | 2022183183 | 2/2022 |
| WO | 2022187821 | 9/2022 |

OTHER PUBLICATIONS

Wang, Hao, "Characteristics of an evaporating thin film in a microchannel", International Journal of Heat and Mass Transfer, 50, 19-20, (2007), 3933-3942.

* cited by examiner

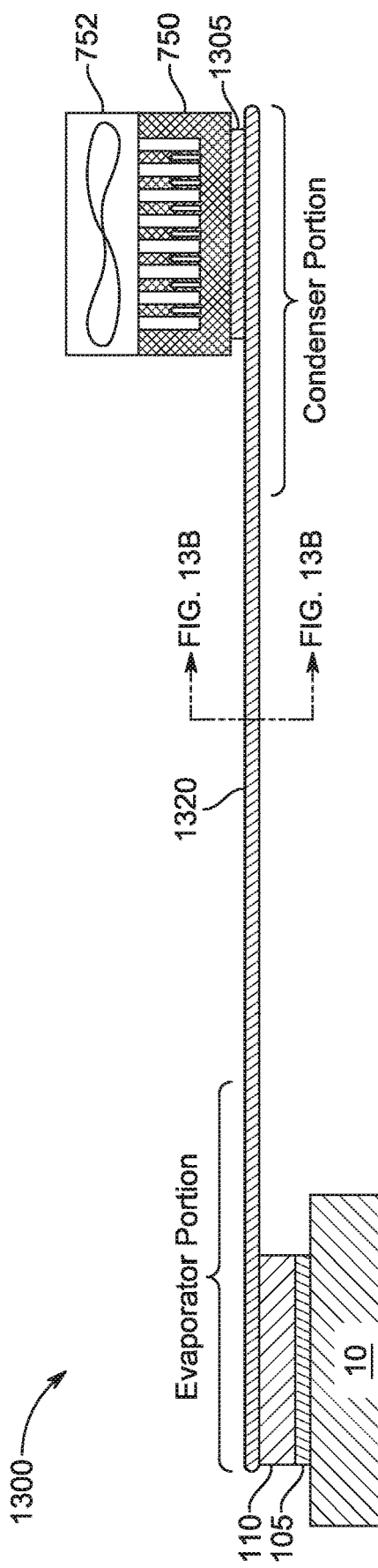
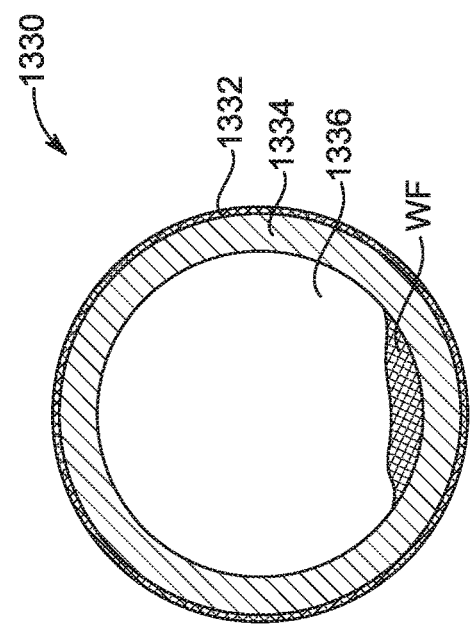
FIG. 13A
FIG. 13B

OCULAR REGION HEAT TRANSFER DEVICES AND ASSOCIATED SYSTEMS AND METHODS

CROSS-REFERENCE TO RELATED APPLICATIONS

The present application claims the benefit of priority to U.S. Provisional Patent Application No. 63/266,400, filed Jan. 4, 2022, and is related to U.S. patent application Ser. No. 17/183,313, titled WEARABLE HEAT TRANSFER DEVICES AND ASSOCIATED SYSTEMS AND METHODS, filed Feb. 23, 2021, now issued as U.S. Pat. No. 11,213,422, and to U.S. patent application Ser. No. No. 18/149,625, titled WEARABLE HEAT TRANSFER DEVICES AND ASSOCIATED SYSTEMS AND METHODS, filed Jan. 3, 2023, the disclosures of which are incorporated herein by reference in their entireties.

TECHNICAL FIELD

This present disclosure relates to heat transfer devices configured to be worn by a human, and associated systems and methods. In some embodiments, the heat transfer devices are configured to be worn around an ocular region of the human.

BACKGROUND

Many types of devices and systems produce significant heat fluxes and there is a growing demand for advanced and efficient systems capable of extracting and dissipating such heat fluxes to keep temperatures within acceptable operating ranges. Many wearable devices, for example, dissipate heat from a target area to reduce pain or swelling, change tissue structures (e.g., reduce adipose tissue and treat skin conditions), or mitigate localized heating of tissue caused by other procedures (e.g., laser treatments). Wearable devices are desirably lightweight and portable, but this presents a challenge for dissipating the significant heat fluxes required in many applications. As a result, a significant gap exists between the required heat transfer performance for many applications and the heat transfer performance of existing devices and systems. For example, current heat transfer systems are often large and heavy to provide adequate heating or cooling for controlling swelling and other post-surgical applications. Therefore, such systems are cumbersome and can be uncomfortable in a wearable device, and they are often too large to work with the complex contours of certain anatomical features. Moreover, heat treatment applications for more sensitive areas, such as under-eye tissue, are limited and unable to provide consistent active cooling treatment for the necessary time duration, which is often needed to freeze and kill corresponding fat cells. As a result, a need exists for an improved wearable heat transfer device.

BRIEF DESCRIPTION OF THE DRAWINGS

Features, aspects, and advantages of the presently disclosed technology may be better understood with regard to the following drawings.

FIG. 13A is a partially schematic side view of a heat transfer device, in accordance with embodiments of the present technology.

FIG. 13B is a partially schematic cross-sectional view of the heat transfer structure shown in FIG. 13A.

Figure 1A:
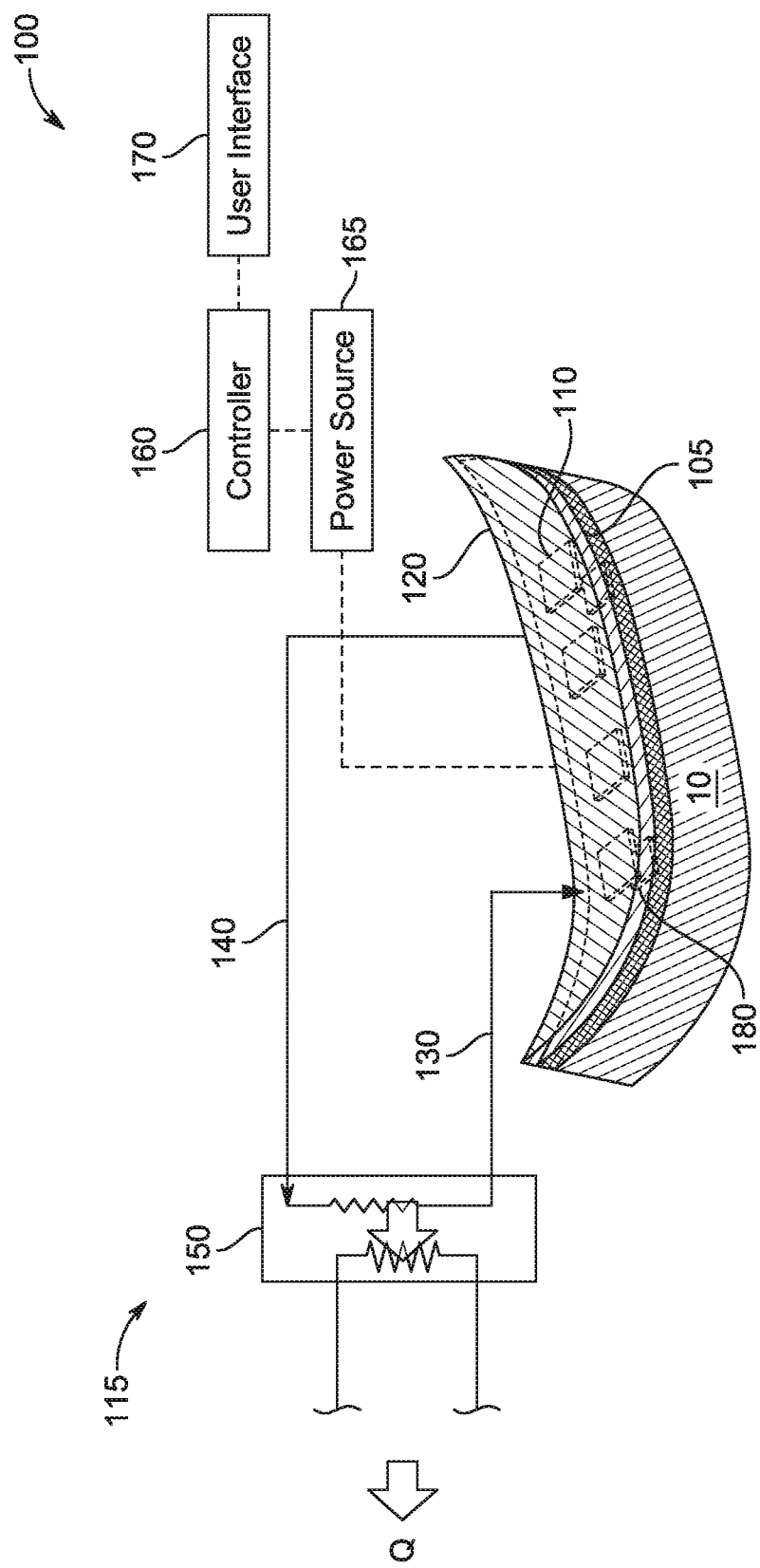
FIG. 1A is a partially schematic isometric view of a heat transfer device, in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

I. Overview

Heat transfer devices generally have potential for efficient thermal management of high heat flux operations, and can have utility in treating different regions of the body. For example, cooling the tissue of humans at the facial or ocular region, or more particularly the under eye tissue, can be an effective treatment for common eye issues, including under eye puffiness, under eye bags, dark circles, and eye hollows, amongst other known issues. For instance, Eye puffiness is the result of periorbital edema and causes fluid buildup under the eye, and can be treated by cooling the area to reduce inflammation. Under eye bags are the result of fat build up under the eyes, and can be treated by a procedure known as cryolipolysis, which applies temperatures less than 5° C. to freeze and kill corresponding fat cells. Dark circles can be eliminated by shrinking the dilated blood vessels under the eyes skin by cooling, which influences vasoconstriction and squeezes down the vessel to reduce the appearance of the dark circles. Round hollows around the eyes arise due to muscle tensions due to long hours working with computers and phones, and cooling around the eyes can relax these muscles and help reduce the pressure on the eyes muscle and consequently eliminates the hollows.

Existing products for treating these and other issues associated with the ocular region have limited and inadequate application. The most prevalent wearable heat transfer devices used to thermally treat such target tissue areas at low temperatures are cold compresses or ice/gel packs, which are often recommended by medical institutions. However, cold compresses have significant shortcomings, including (i) the lack of temperature control at which the tissue is exposed, (ii) a limited capacity for cooling or limited ability to cool for the necessary duration of time, (iii) an inability to provide continuous cooling therapy without adjusting or tending to the device, and (iv) a lack of flexibility of the device, e.g., due to the rigidness of the icepacks, therein causing an uncomfortable fit for the user or human. This last shortcoming can further limit the amount of heat transfer between the device and human, as the inflexible nature and bulkiness of the device prevents a conforming fit which makes contact with the under eye area difficult, unreliable, and inefficient. As a result, these and other wearable devices for treating the facial or ocular region are inadequate and generally ineffective in treating underlying conditions (e.g., pain, swelling, overheating, diminished blood perfusion, etc.).

Embodiments of the present disclosure address at least some of the above-described issues by providing thermal management and/or heat transfer devices and systems that, amongst other features, allow for better temperature control, and enable enhanced thermal contact between the device and the human, e.g., by being flexible, lighter and thinner than current related devices. For example, as described in additional detail herein, embodiments of the present disclosure can include heat transfer devices including (i) a thermoelectric component (TEC) including a first side configured to be operated at a first temperature and a second side, opposite the first side, configured to be operated at a second temperature greater than the first temperature; (ii) a contact member thermally coupled to the TEC; and (iii) a heat transfer system configured to distribute heat from the TEC. The heat transfer system can include a heat transfer structure thermally coupled to the TEC, a cold fluid passage fluidically coupled to the heat transfer structure, a hot fluid passage fluidically coupled to the heat transfer structure, and a heat exchanger (e.g., an air-cooled heat exchanger) thermally coupled to the heat transfer structure. The contact member, TEC, and heat transfer system can be incorporated onto a rigid frame such that, when the rigid frame is worn by a human or user, the contact member is able to thermally treat a desired target area. In doing so, embodiments of the present disclosure enable the target area of the human to undergo, e.g., rapid and controlled cooling and thereby treat certain underlying conditions of the ocular region.

Embodiments of the present disclosure can further include an inflatable interface positioned adjacent the contact member. When inflated, the inflatable interface applies pressure toward the contact member, which can enable better heat transfer between the contact member and the desired area. In some embodiments, the pressure of the inflatable interface can be set to maintain a particular contact pressure on the target area, or can be varied between alternating pressures to induce a massage sensation during thermal treatment.

As used herein, the term "thermally coupled" can mean directly or indirectly thermally coupled. For example, a first component and a second component may be thermally coupled to one another, despite being spaced apart, if heat supplied from the first component is in some way distributed to the second component. As such, the term "thermally coupled" should not be limited to require that heat emitted from the first component be directly absorbed by the second component.

In the Figures, identical reference numbers identify generally similar, and/or identical, elements. Many of the details, dimensions, and other features shown in the Figures are merely illustrative of particular embodiments of the disclosed technology. Accordingly, other embodiments can have other details, dimensions, and features without departing from the spirit or scope of the disclosure. In addition, those of ordinary skill in the art will appreciate that further embodiments of the various disclosed technologies can be practiced without several of the details described below.

II. Heat Transfer Devices and Associated Systems and Methods

Figure 1B:
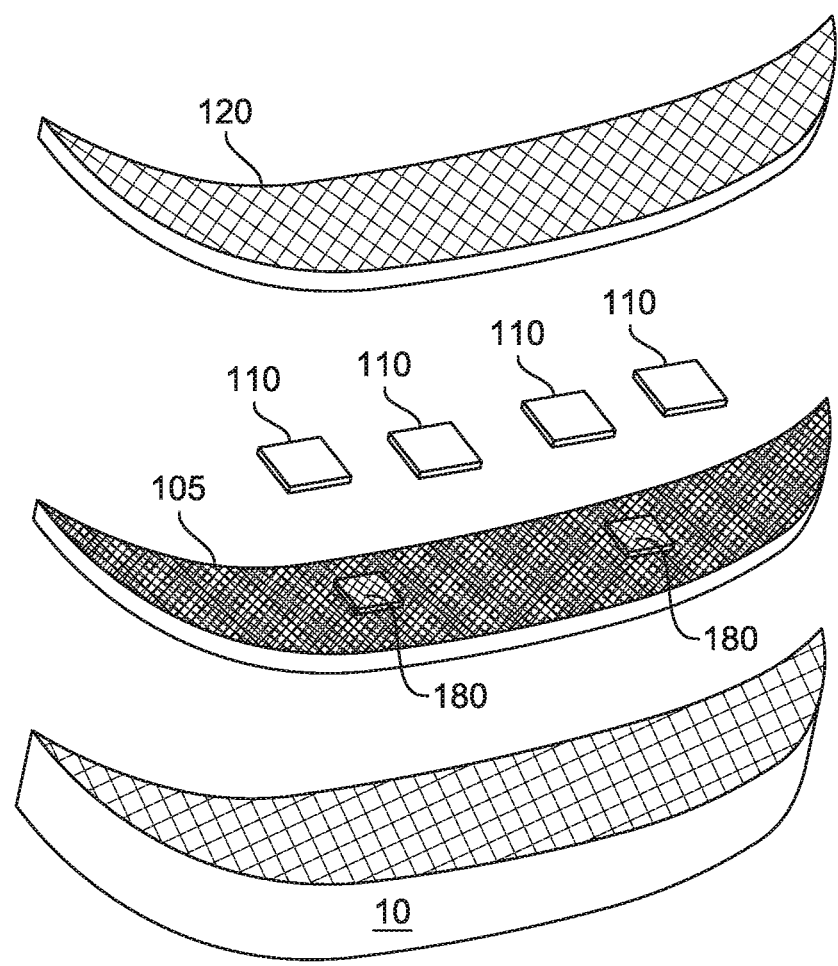
FIG. 1B is an exploded view of a portion of the heat transfer device shown in FIG. 1A.

FIG. 1A is a partially schematic cross-sectional side view of a heat transfer device 100 ("device 100") configured to be disposed over a portion of a mammal or human 10 ("human 10"), and FIG. 1B is an enlarged partially schematic cross-sectional isometric view of a portion of the device 100. Referring to FIGS. 1A and 1B together, the device 100 includes (i) a contact member 105 over a portion or target area (e.g., skin, tissue, head, face, or other body part area) of the human 10, (ii) thermoelectric components or modules 110 ("TECs 110") over the contact member 105 and thermally coupled to the human 10, and (iii) a heat transfer system 115 thermally coupled to and configured to remove heat from the TECs 110. The heat transfer system 115 can be a closed loop system, and can include (i) a heat transfer structure 120 over and thermally coupled to the TECs 110, (ii) a heat exchanger 150, (iii) a cooled or second fluid distribution passage 130 ("cold fluid passage 130") (e.g., a conduit, tubing, or piping) configured to direct a cooled working fluid toward the TECs 110 and away from the heat exchanger 150, and (iv) a heated or first fluid distribution passage 140 ("hot fluid passage 140") (e.g., a conduit, tubing, or piping) configured to direct a heated working fluid away from the TECs 110 and toward the heat exchanger 150 (e.g., for cooling). The heat exchanger 150 can be cooled passively or actively (e.g., via a fan or separate cooling source) to remove heat (Q) provided via the heated working fluid. As described in additional detail herein the heat transfer system 115 can include a single-phase heat transfer system or a two-phase heat transfer system (e.g., an evaporative cooling system or pool boiling system). For embodiments including the two-phase heat transfer system, the heat transfer structure 120 can be an evaporator, the heated working fluid can be a vapor, the cooled working fluid can be a liquid, and the heat exchanger 150 can be a condenser.

As shown in FIG. 1A, the device 100 further includes a controller 160, a power source 165 in electrical communication with the TECs 110 and configured to be controlled by the controller 160, a user interface 170 in electrical communication with the controller 160, and one or more temperature sensors 180 in electrical communication with the controller 160. In operation, the controller 160 regulates the amount of current sent from the power source 165 to TECs 110 based on a desired set temperature for the TECs 110, which are configured to heat and/or cool the target area of the human 10. The temperature sensors 180 can be positioned to detect a temperature of the target area of the human 10 and provide feedback to the controller 160 to determine any deviance from the desired temperature, which the controller 160 can use to make necessary adjustments to the current provided to the TECs 110. When the device 100 is in a cooling mode, for example, heat transfers from the human 10 to the contact member 105, to the individual TECs 110, and to the heat transfer system 115. As heat is removed from the human 10 in such a manner, a cooling zone on the target area forms and can extend to a cooling depth of the human 10, which can be at least 1 millimeter (mm), 2 mm, 3 mm, 4 mm, or 5 mm, or within a range of 1-5 mm or any incremental range thereof (e.g., 1.5 mm or 2.1-3 mm). The cooling zone can correspond to a heating zone when the device 50 is in a heating mode. As explained in additional detail herein, cooling (or heating) the target area in such a controlled manner can enable the device 100 and other embodiments of the present technology to efficiently thermally treat target areas in ways current conventional heat transfer devices cannot.

In some embodiments, the heat transfer system 115 can include one or more pumps, and flow of the working fluid through the heat transfer system 115 is driven by the pumps. In other embodiments, flow of the working fluid through the heat transfer system 115 (e.g., a two-phase heat transfer system) is driven by gravity. For example, when driven by gravity, the heat exchanger 150 may be positioned physically above the other portions (e.g., the heat transfer structure 120) of the heat transfer system 115 such that gravity can provide enough head pressure to circulate the working fluid to the heat transfer structure 120. Additionally or alternatively, as explained in more detail herein, flow of the working fluid through the heat transfer system 115 can be driven by capillary forces induced by microfeatures (e.g., pillars, pins, or walls) that form channels, present within chambers of the heat transfer structures that drive the liquid phase of the working fluid from inlets of the chambers toward the outlets of the chambers. Additionally or alternatively, in some embodiments the heat transfer system 115 includes a buffer vessel or reservoir configured to hold an excess amount of working fluid, e.g., to ensure the supply of the working fluid can be continuously supplied and does not run out. The buffer vessel can be particularly beneficial when the device 100 is operating at more extreme temperatures (e.g., 45° C., −20° C., etc.). In some embodiments the buffer vessel and the heat exchanger 150 may comprise a single integral unit.

The contact member 105 is thermally coupled to each of the TECs 110, and extends between and/or over each of the TECs 110. The contact member 105 can comprise a thermally conductive and/or semi-rigid contact member that acts as a heat spreader to enhance heat transfer to and/or from the target area of the human 10 at least in the regions between the TECs 10. Additionally or alternatively, the contact member 105 can comprise conductive materials and/or biocompatible materials, including metals, metallic alloys, coatings, polymers, silicone, and/or combinations thereof. In some embodiments, the contact member 105 can comprise biocompatible adhesives e.g., to retain the device 100 relative to the target area. In some embodiments, the contact member 105 comprises a metal sheet or material at a first side of the contact member 105 and in contact with the individual TECs 110, and a non-metal sheet or material at a second opposing side of the contact member 105 and in contact with the human 10. In some embodiments, the contact member 105 is expandable (e.g., stretchable). As shown in FIGS. 1A and 1B, the TECs 110 are each disposed over the contact member 105. In some embodiments, the contact member 105 extends only between individual ones of the TECs 110 and the TECs 110 are disposed directly over the human 10 (e.g., in direct contact with the human 10). In some embodiments, the contact member 105 can be omitted entirely, and the TECs 110 are over or directly over the human 10.

The TECs 110 can comprise a semiconductor-based electronic component configured to move heat from one side of the TEC 110 to a second opposing side of the TEC 110. The TECs 110 can provide precise, controllable, and/or localized temperature control at the interface between the target area and the device 100. The TECs 110 can be set to a particular temperature and/or predetermined temperature profile (e.g., constant temperature profile, temperature cycle profile, and/or time-based profiles) by the controller 160 to cool and/or heat the adjacent target area of the human 10. Setting the TECs 110, e.g., to a particular temperature can include providing a current to the TECs 110 via the power source 165 that corresponds to that temperature.

In some embodiments, individual TECs 110 are individually controlled by the controller 160. For example, the individual TECs 110 can be controlled independent of other individual TECs 110, e.g., to provide localized and variable control when desired. As such, when the device 100 is disposed such that the contact member 105 is thermally coupled to the human 10, different regions of the device 100 can be heated and/or cooled at different temperatures depending on the desired therapy for the individual region. For example, when the device 100 is wrapped around an arm or leg, individual TECs 110 or groups of TECs 110 adjacent a bone region may be set to a first temperature, and other TECs 110 or other groups of TECs 110 adjacent a more muscular region may be set to a second temperature (e.g., higher than the first temperature). In doing so, the human 10 can experience desired therapy at only certain target areas.

As an example of how the TECs 110 can be operated, in some embodiments the first side of the TECs 110 facing the human 10 or the second side of the TECs 110 facing the heat transfer structure 120 can be set to a temperature within a range of 45° C. to −20° C. (e.g., 40° C., 35° C., 20° C., 5° C., 0° C., −5° C., −10° C., −15° C., etc.). In some embodiments, the TECs 110, either alone or in combination with the evaporators 120, can be configured such that the second side of the TECs 110 is set or held at a first temperature or first temperature range and the first side of the TECs 110 are controlled to be cooled from normal surface body surface temperatures to a second temperature or second temperature range. In such embodiments, the second temperature or second temperature range can be more or less (e.g., 5° C., 10° C., 20° C., 30° C., or 40° C. more or less) than the first temperature or first temperature ranges. Additionally or alternatively, upon setting the temperature at the second side of the TECs 110, the first side of the TECs 110 can be configured to reach a desired temperature within a predetermined time, e.g., no more than 10 seconds, 20 seconds, 30 seconds, 40 seconds, or 60 seconds, or within a range of 10-60 second or any incremental range therebetween. As disclosed herein, operation of the TECs 110 may be based on a signal received from the temperature sensor(s) 180, which are configured to detect temperature of the target area, the first side of the TECs 110, or the second side of the TECs 110.

The TECs 110 can be placed in a heating mode, a cooling mode, or a mode that cycles between cooling and heating to control the temperature at the target area. Heat flow across an individual TEC 110 can be a function of temperature difference between its two side and/or the electric power input provide to the individual TEC 110 from the power source 165. The mode and/or operation of the mode can be selected based on, e.g., predetermined cycle times and/or feedback from the temperature sensor 180. When in the heating mode, the TECs 110 can provide heat to the target area of the human 10 (e.g., via the contact member 105) by heating the first side of the TECs 110 which causes the second sides of the TECs 110 to cool. The heat transfer structures 120 can be controlled (e.g., turned off) to mitigate further cooling of the second side of the TECs 110. In some embodiments, the device 100 can further comprise additional resistive heaters that can be controlled via the controller and configured to heat the adjacent target area of the human 10.

When in the cooling mode, the heat transfer structures 120 are configured to remove heat from hotter second sides of the TECs 110 and thereby enable the opposing first sides of the TECs 110 to cool the adjacent target area of the human 10. As such, in the cooling mode heat flows from the target area of the human 10 in a radially outward direction to the TECs 110 and then to the heat transfer structures 120. As previously described, the TECs 110 can also cycle between the cooling and heating modes, which can enhance blood flow and perfusion to the target area. In some embodiments, parameters of the cooling and/or heating modes are based on or limited by safety considerations, such as a maximum heating or cooling temperature and/or maximum amount of heating or cooling time (e.g., 15 minutes, 20 minutes, etc.). Additional details regarding individual TECs 110 are provided herein (e.g., with reference to FIGS. 3 and 4).

As shown in the illustrated embodiment, the device 100 includes four separate TECs 110. In other embodiments, the actual number of TECs 110 may be more or less (e.g., 2, 3, 5, 10, 20, 30, or more) depending on the particular end use of the device 100 and the heating/cooling capacity requirements needed from the device 100. Additionally or alternatively, the TECs 110 may be arranged differently than that shown in FIGS. 1A and 1B. For example, in addition to individual TECs 110 be disposed in a row, individual TECs 110 may be disposed around a target area (e.g., around a circumference of the human 10) or stacked on top of one another to increase the heating and/or cooling ability of that particular stack of TECs 110. In such embodiments, a second TEC 110 stacked on top of a first TEC 110 can have one side in contact with the first TEC 110 and another opposing side in contact with the heat transfer structure 120. The stacked arrangement of TECs 110 can be particularly beneficial when more extreme temperatures (e.g., less than 0° C., −10° C., or −20° C.) at the target area of the human 10 are desired. This ability to vary the number and arrangement of TECs 110 enables the device 100 to be tailored to a greater variety of end use applications.

As shown in FIGS. 1A and 1B, the heat transfer structure 120 is over multiple TECs 110. However, in some embodiments, as described herein, the heat transfer structure 120 is over a corresponding single TEC 110 and each heat transfer structure 120 is fluidically coupled to the hot fluid passage 140 and cold fluid passage 130. For example, for an individual heat transfer structure 120, the working fluid is supplied from the cooled distribution passage 130 to an inlet (e.g., one of a plurality of inlets) of the heat transfer structure 120. As the working fluid flow through the heat transfer structure 120, the working fluid absorbs heat from the corresponding TEC 110 and is directed through an outlet 142 (e.g., one of a plurality of outlets) of the heat transfer structure 120 to the hot fluid passage 140. The hot fluid passage 140 and the cold fluid passage 130 are each fluidically coupled to the heat exchanger 150 and are part of a closed loop system. The heat exchanger 150 can be spaced apart from the heat transfer structure 120 and/or the target area of the human 10, where space is limited. Additionally, spacing apart the heat exchanger 150 in such a manner can enable the heat exchanger to be larger, thereby enabling more heat transfer, and/or ensure the heat exchanger 150 does not impede the comfort or fit of the device 100 when worn by the human 10. In some embodiments, the heat exchanger is radially peripheral to each of the hot fluid passage 140 and the cold fluid passage 130. Additionally or alternatively, the heat exchanger can be physically above the heat transfer structure120 such the working fluid provided from the heat exchanger 150 has additional head pressure, which can beneficially provide better circulation of the working fluid through the heat transfer structure 120.

The closed loop system illustrated and described with reference to FIG. 1A and elsewhere herein enables embodiments of the present technology to provide the enhanced thermal treatment (e.g., enhanced cooling) relative to the conventional heat transfer devices. Additionally, the closed loop system of embodiments of the present technology mitigates the issues often present with inferior devices, such as overheating, dry-out, and the like.

The sensors 180 can be configured to measure a desired parameter (e.g., temperature, pressure, etc.) of the contact member 105, individuals TECs 110, and/or the target area. Each of the sensors 180 can be in communication with the controller 160 and be used to verify and/or improve safety (e.g., prevent overcooling and/or high pressure zones), efficacy, and operation of the device 100 via the controller 160.

As previously described, the controller 160 can be configured to operate the device 100 in one of a plurality of operating modes (e.g., a cooling mode, a heating mode, or both), and/or provide a process value (e.g., a set temperature) at which the device 100 is configured to operate. The controller 160 can provide a setpoint temperature within a range of 40° C. to −20° C. (e.g., 35° C., 20° C., 0° C., −10° C., etc.) to the device 100 such that the TECs 110 (e.g., the first or second side of the TECs) are configured to operate at the setpoint temperature. Additionally or alternatively, the controller 160 can be configured to receive inputs from the sensors 180 on the device 100 and control the device 100 based on the received inputs. For example, the controller 160 can determine any abnormalities of the device 100 and automatically generate indications of the abnormalities and/or adjust the operating parameters of the device 100. Additionally or alternatively, the controller 160 may utilize artificial intelligence and/or machine learning to adjust power and/or other control parameters, e.g., based on previous treatments used for the same human or a group of humans.

The user interface 170 can include a display, and/or an application or program that enables the human 10 to utilize the device, e.g., through a mobile device (e.g., a phone, tablet, watch, laptop, etc.) or other computing device. The user interface 170 can include pre-programmed thermal management procedures and/or enable the human 10 to adjust cooling and heating parameters based on a desired application.

Figure 2A:
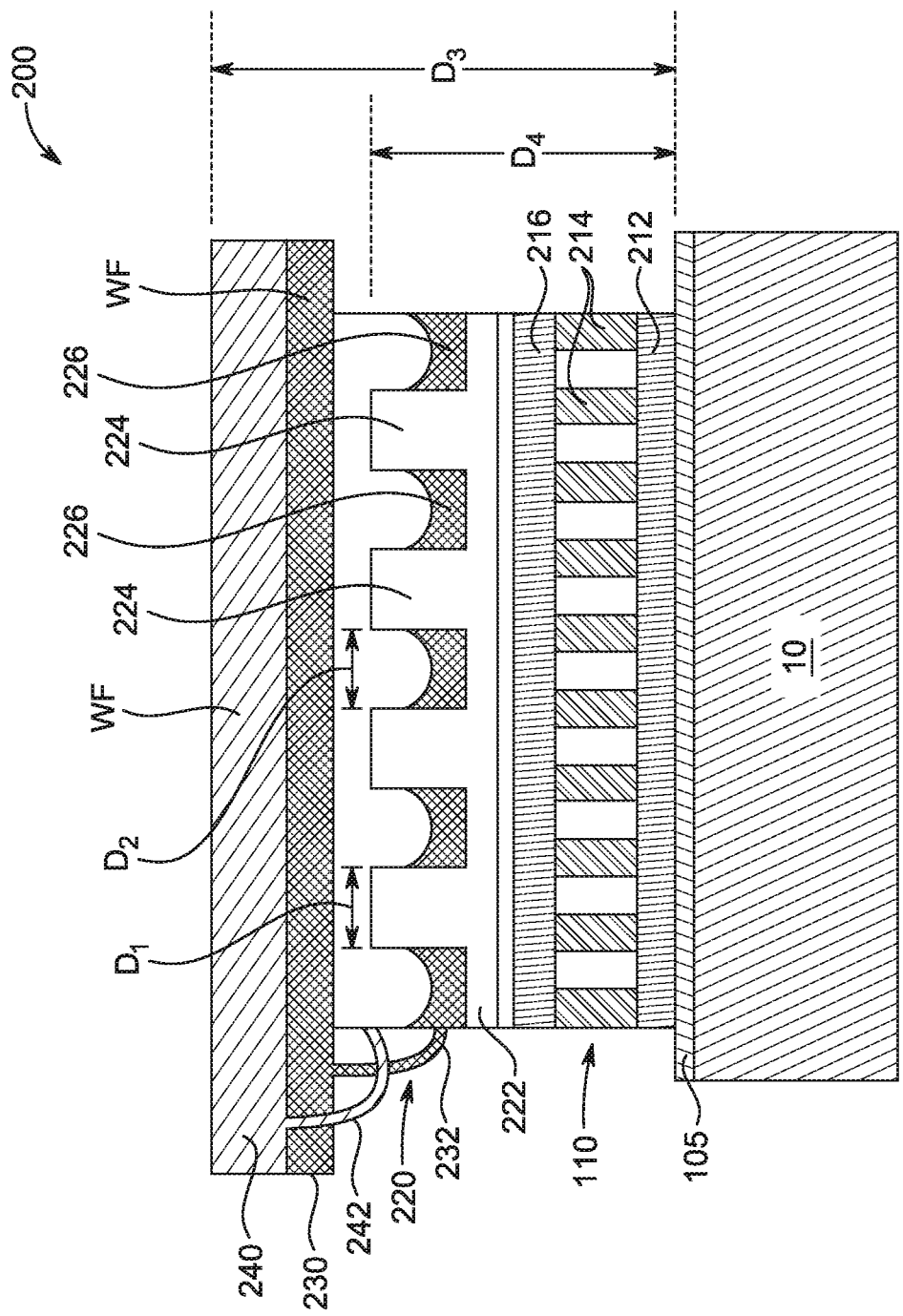
FIG. 2A is a partially schematic cross-sectional view of a portion of a heat transfer device, in accordance with embodiments of the present technology.
Figure 2B:
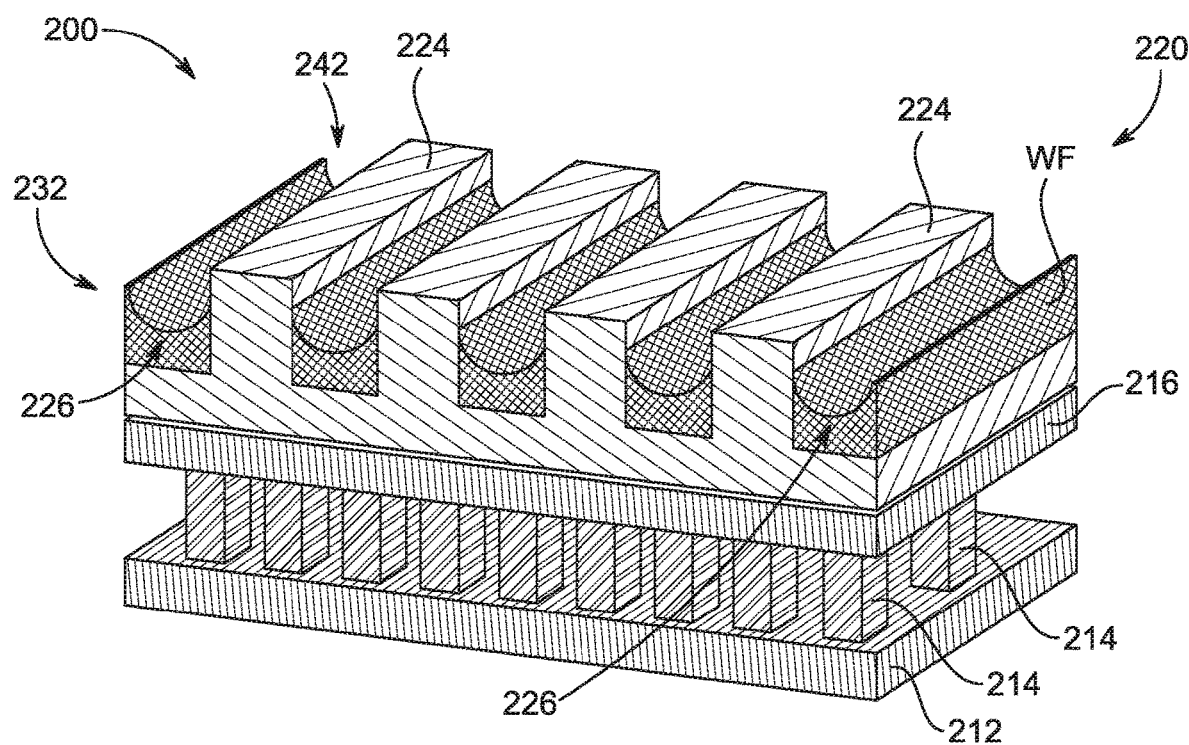
FIG. 2B is a partially schematic isometric view of a portion of the heat transfer device shown in FIG. 2A.

FIG. 2A is a partially schematic cross-sectional view of a portion of a heat transfer device 200 ("device 200"), and FIG. 2B is a cross-sectional isometric view of a portion of the device 200. The device 200 can be a two-phase heat transfer device or a single-phase heat transfer device, and generally corresponds to and includes many features similar or identical to those of the device 100 (FIGS. 1A and 1B). For example, as shown in FIG. 2A, the device 200 includes the contact member 105 and the TEC 110 previously described, as well as a heat transfer structure 220 (e.g., the heat transfer structure 120), a cold fluid passage 230 (e.g., the cold fluid passage 130) fluidically coupled to the individual heat transfer structure 220 via an inlet region 232, and a hot fluid passage 240 (e.g., the hot fluid passage 140) fluidically coupled to the individual heat transfer structure 220 via an outlet region 242. The cold fluid passage 230 and hot fluid passage 240 are fluidically coupled to a heat exchanger (e.g., the heat exchanger 150; FIG. 1A), which has been omitted from FIG. 2A. The heat transfer structure 220, cold fluid passage 230, hot fluid passage 240, and other components (e.g., the heat exchanger) can together comprise a heat transfer system. The heat transfer structure 220 and TEC 110 illustrated in FIG. 2A correspond to a single module that can be one of modules of the device 200.

The device 200 illustrates certain features not viewable in FIG. 1A or 1B. For example, as shown in FIG. 2A, the TEC 110 of the device 200 includes a thermoelectric first face 212 at a first side of the TEC 110 and adjacent the contact member 105, a thermoelectric second face 216 at a second opposing side of the TEC 110 and adjacent the heat transfer structure 220, and thermoelectric legs or pillars 214 extending between the first face 212 and the second face 216. In some embodiments, the second face 216 may be omitted and the legs 214 are in direct contact with the heat transfer structure 220. As shown in FIG. 2A, the TEC 110 and the heat transfer structure 220, cold fluid passage 230, and hot fluid passage 240 can have a dimension (D3) of no more than 1 mm, 3 mm, 5 mm, 10 mm, 15 mm, 25 mm, or 30 mm, or within a range of 1 millimeter (mm) to 30 mm or any incremental range therebetween, and the TEC 110 and the heat transfer structure 220 can have a dimension (D4) greater than a dimension (D3), of no more than 1 mm, 3 mm, 5 mm, 10 mm, 15 mm, 25 mm, or 30 mm, or within a range of 1 mm to 30 mm or any incremental range therebetween.

In some embodiments, the TECs 110 (e.g., the first face 212, the second face 216, and/or the legs 214) can comprise a rigid material that is generally inflexible. In such embodiments it can be desirable to limit the footprint of individual TECs 110 to maintain the overall flexibility of the device 200 (or any other heat transfer device disclosed herein) and ensure it can conform around or to the geometry of a target area (e.g., the ocular region). That is, by limiting the footprint of the TECs 110 in such embodiments, and therein the rigid portions of the device 200, the device 200 can have sufficient flexibility, e.g., from the contact member 105, to conform around or to the geometry of a target area to improve thermal contact between the human 10 and the TECs 110 of the device 200. In some embodiments, the TECs 110 can have a footprint (e.g., over the contact member 105) of no more than 2 $mm^2$, 3 $mm^2$, 4 $mm^2$, 5 $mm^2$, 6 $mm^2$, 7 $mm^2$, 8 $mm^2$, or 9 $mm^2$ or within a range of 2-9 $mm^2$ or any incremental range therebetween.

In some embodiments, the first face 212, the second face 216, and/or the legs 214 of individual TECs 110 can comprise a flexible material, e.g., to enable the TECs 110 to better conform to a target area when the device 200 is worn by a human 10. Relative to those embodiments in which the TECs 110 are formed of rigid materials, using a flexible material, e.g., for the first face 212 (i.e., the hot side) of the TEC 110 can enable the footprint of the TEC 110s to be larger since the flexibility of the device 200 is no longer limited by the TECs 110. In doing so, the larger heat TECs 110 can enable a higher capacity for heat transfer and/or decrease manufacturing costs for the device 200.

As shown in FIG. 2A, the heat transfer structures 220 can include a chamber 220, a base substrate or member 222 within the chamber 220, microfeatures 224 that protrude from the base member 222, and channels 226 formed between and defined by adjacent ones of the microfeatures 224. The heat transfer structure 220 can comprise an integral structure (e.g., a single component) and thus include a continuous surface extending along the base member 222 and the channels 226. As shown in FIG. 2, the working fluid (WF) is disposed within the channels 226 and can form a meniscus, which is due in part to the properties of the working fluid (WF) and the microfeatures 224, or more particularly the heat of the microfeatures 224 and arrangement (e.g., spacing) of the microfeatures 224 relative to one another. Without being bound by theory, the meniscus can form a thin film portion at an interface with the adjacent microfeature walls that enhances evaporation for two-phase heat transfer systems and/or heat transfer from the TECs 110 to the heat transfer structure 120, and then to the working fluid (WF). In operation, the heat and/or arrangement of the microfeatures 224 induce capillary forces to the working fluid (WF), causing the liquid to move from the inlet region 232 at a first end of the chamber 220 to the outlet region 242 at a second opposing end of the chamber 220 where it exits as a heated working fluid (WF) (e.g., a vapor or heated liquid). Individual microfeatures 224 can have a lateral dimension (D1) of 5 microns, 10 microns, 20 microns, 50 microns, 100 microns, 200 microns or 250 microns, or within a range of 5-250 microns or any incremental range therebetween. The microfeatures can be spaced apart from adjacent microfeatures 224 by a lateral dimension (D2) of 5 microns, 50 microns, 10 microns, 200 microns, 400 microns, 500 microns or 1000 microns, or within a range 5-1,000 microns.

As shown in FIG. 2A, the microfeatures 224 extend from the base member 222 away from the TECs 110. In other embodiments, the heat transfer structure 220 can be disposed in an opposite orientation with the base member 222 being adjacent the cooled working fluid passage 130 and the microfeatures extending from the base member 222 toward the TECs 110. In such embodiments, the heat transfer structure 220 can include a reservoir adjacent the TEC 110 and containing the working fluid (WF), and end portions of the microfeatures 224 are submerged within the working fluid (WF). In operation, the microfeatures 224 induce capillary forces on the liquid working fluid (WF) and generate heated working fluid (WF) (e.g., vapor) that escapes the chamber 220 and collects in the heated working fluid passage 240.

As described above, the device 200 of FIG. 2A can be a two-phase heat transfer device or a single-phase heat transfer device. When operating as a single-phase heat transfer device, the working fluid remains as liquid throughout the closed-loop heat transfer system, transitioning between a cooled working fluid provided from the heat exchanger to the heat transfer structure 220 and a heated working fluid provided from the heat transfer structure 220 to the heat exchanger. As such, when operating as a single-phase heat transfer device, the heated working fluid is supplied from the liquid reservoir of working fluid within the channels 426 of the heat transfer structure 220 to the heated working fluid passage 240.

FIG. 2B is a cross-sectional isometric view of a portion of the heat transfer device 200 of FIG. 2A. Only the TEC 110 and heat transfer structure 220 are shown in FIG. 2B, and other elements of the device 200 are omitted for illustrative purposes. As shown in FIG. 2B, the heat transfer structure 220 include the microfeatures 224 defined by continuous elongated walls that form continuous elongated channels 226 arranged in multiple rows. The channels 226 can be substantially identical to one another and have a uniform width along its length. In some embodiments, the channels 226 can have widths that vary along their length, e.g., becoming narrower as they approach an inlet or outlet of the chamber. Additionally or alternatively, individual channels may differ (e.g., be wider or narrower) than adjacent channels. Without being bound by theory, such channel design can induce additional favorable pressure gradients on liquid working fluid flow.

Figure 3:
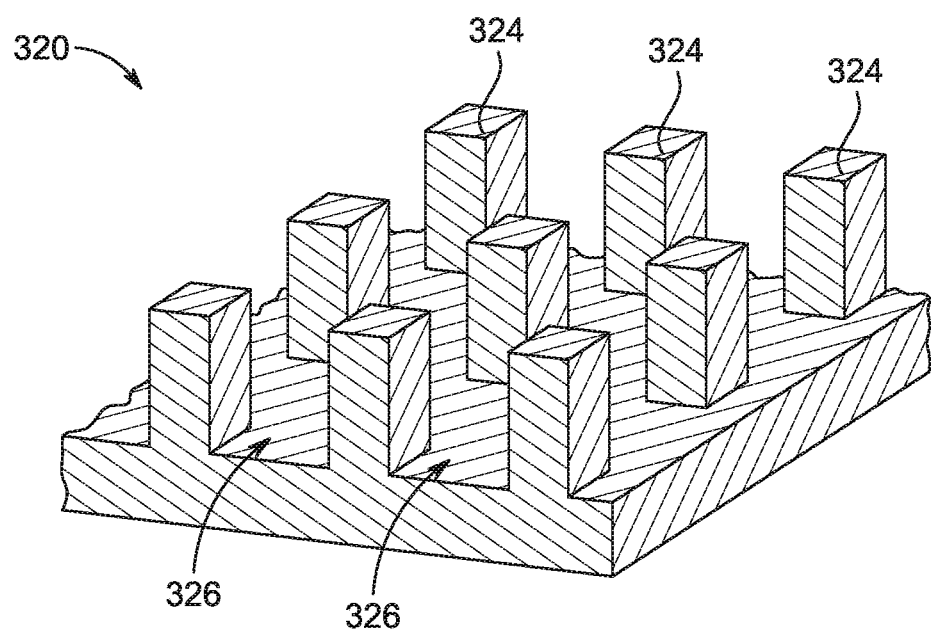
FIG. 3 is a partially schematic isometric view of a heat transfer structure of a heat transfer device, in accordance with embodiments of the present technology.

In some embodiments, the microfeatures 224 of the heat transfer structure 220 can include different shapes. For example, as shown in FIG. 3, which is a cross-sectional view of a portion of a heat transfer structure 320, the heat transfer structure 320 includes microfeatures 324 that are pillars or pins arranged in rows and columns, or other suitable arrangements that define channels 326 in the spaces between the microfeatures 324. While the pin-type microfeatures 324 shown in FIG. 3 have a rectilinear cross-section, in some embodiments the microfeatures 324 can have circular or other cross-sectional shapes (e.g., hexagonal, octagonal, etc.).

Figure 4A:
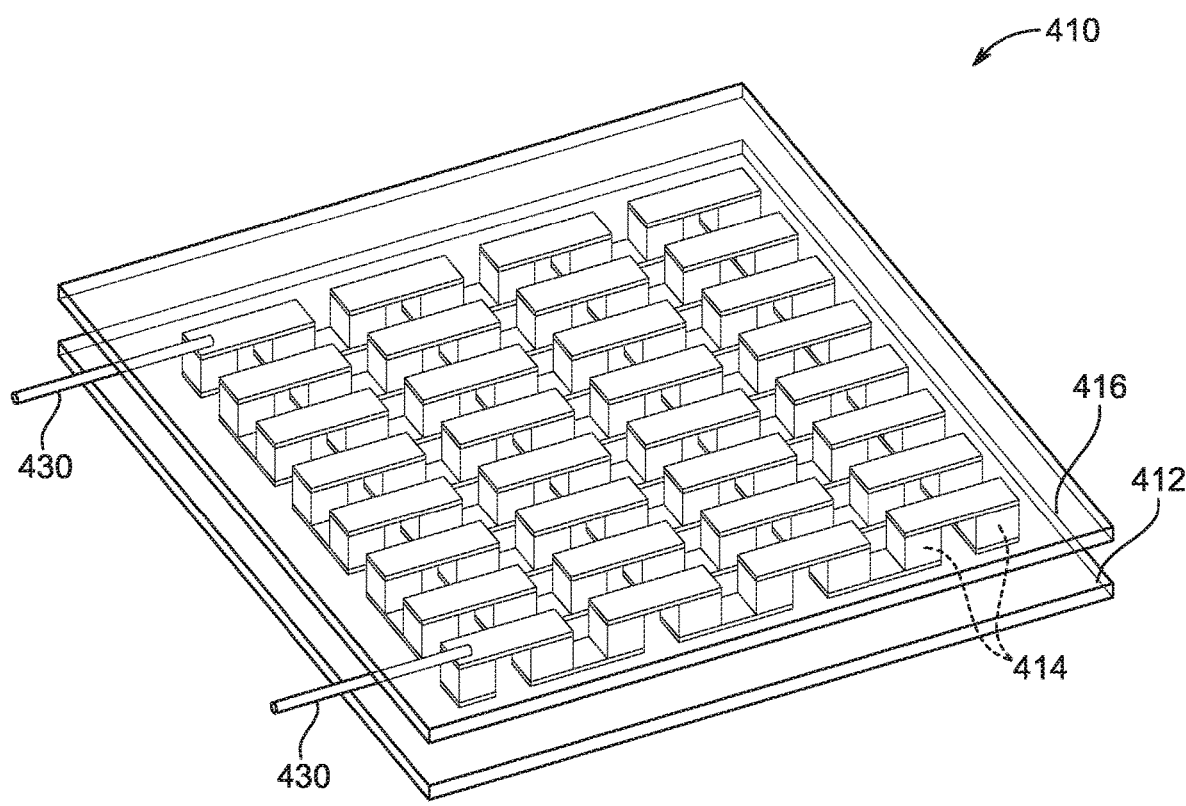
FIGS. 4A and 4B are partially schematic isometric views of a thermoelectric component, in accordance with embodiments of the present technology.
Figure 4B:
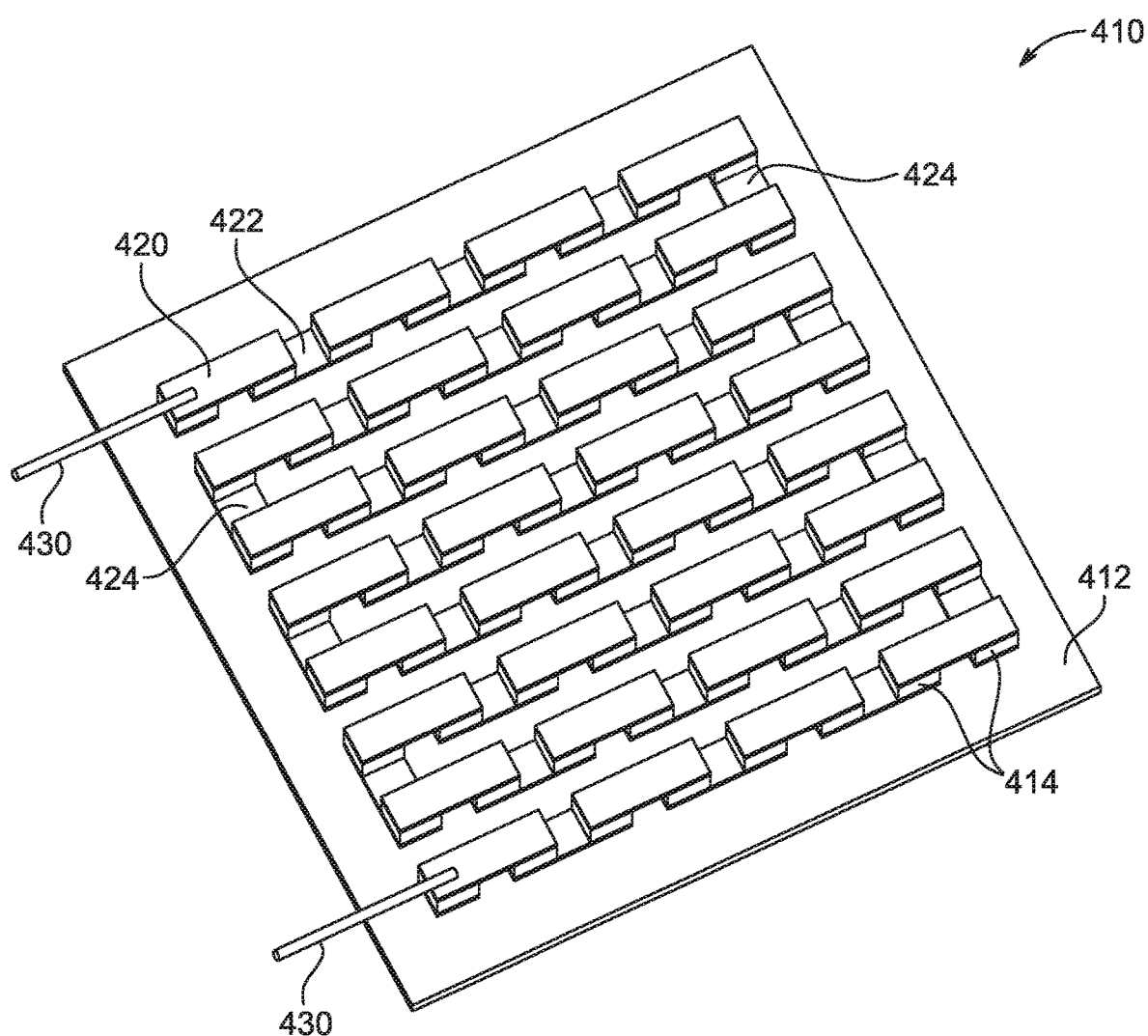

As previously described, the TECs of the heat transfer devices can be flexible and/or comprise a flexible material, which can enable the TECs to bend and better conform to a target area of the human and therein provide better heat transfer from the TECs. FIGS. 4A and 4B, which are partially schematic isometric views of a TEC 410, illustrate one such embodiment. The TEC 410 can correspond to the TEC 110 referred to herein. Referring to FIGS. 4A and 4B together, the TEC 410 includes a thermoelectric first face 412 (e.g., the thermoelectric first face 212; FIG. 2A) at a first side of the TEC 410, a thermoelectric second face 416 (e.g., the thermoelectric second face 212; FIG. 2A) at a second opposing side of the TEC 410, and thermoelectric legs or pillars 414 (e.g., the thermoelectric pillars 412; FIG. 2A) extending between the first face 412 and the second face 416. One or both of the thermoelectric first face 412 and the thermoelectric second face 416 can be made of a flexible material and/or be thin enough to have a degree of flexibility. The TEC 410 is electrically connected to a power source via couplers 430, e.g., extending from the first thermoelectric face 412.

As shown in FIG. 4B, which omits the thermoelectric second face 416 for illustrative purposes, the TEC 410 includes conductive members 420, 422, 424 extending between and electrically coupling adjacent thermoelectric pillars 414. The conductive members 420 can extend over and between top surfaces of the thermoelectric pillars 414 proximate the thermoelectric second face 416, the conductive members 422 can extend between bottom surfaces of the thermoelectric pillars 414 proximate the thermoelectric face 416 in a first direction parallel to a row of the thermoelectric pillars 414, and the conductive members 424 can extend between bottom surfaces of the thermoelectric pillars 414 proximate the thermoelectric face 416 in a second direction parallel to a column of the thermoelectric pillars 414. The conductive members 420, 422, 424 can comprise copper (e.g., braided copper wire) or other metal that is flexible and conductive.

The flexibility of the TEC 410, or more specifically the flexibility of the thermoelectric first face 412, the thermoelectric second face 416, and/or the conductive members 420, 422, 424, can enable the TEC 410, and corresponding device generally, to better conform around the contact member (e.g., the contact member 105; FIG. 1A) or component in direct contact with the target area of the human. In doing so, the TEC 410, relative to a rigid TEC, can have better heat transfer with the contact member and, therein, with the target area.

Figure 5:
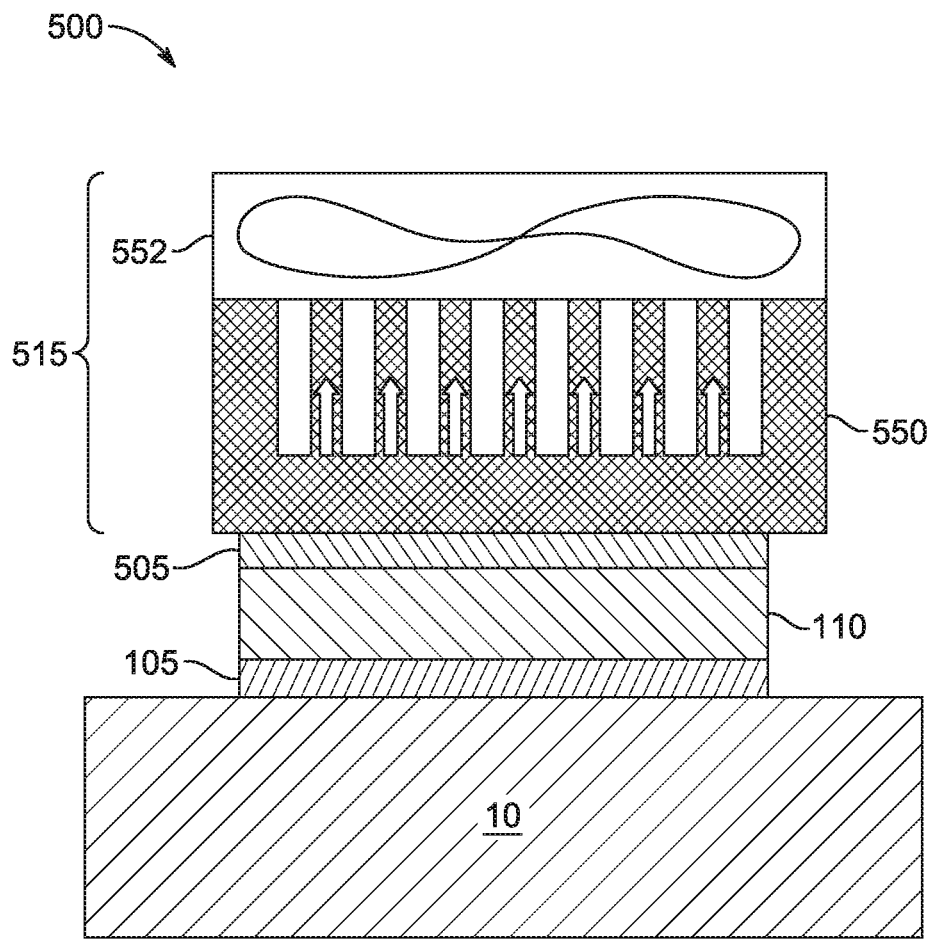
FIG. 5 is partially schematic side view of a heat transfer device, in accordance with embodiments of the present technology.

FIG. 5 is a partially schematic cross-sectional view of a heat transfer device 500 ("device 500"), in accordance with embodiments of the present technology. The device 500 can include the contact member 105 over the human 10, and the TEC 110 over the contact member 105 and thermally coupled to the human 10, as previously described. The device 300 can further comprise a heat transfer system 515 including a heat spreader 505 over and thermally coupled to a hot face of the TEC 110, a heat exchanger 550 over the heat spreader 505, and a fan over the heat exchanger 550 and configured to removed heat from the heat exchanger 550. The heat exchanger 550 can include fins or other elongate structures that increase surface area exposure to improve heat transfer. In some embodiments, the heat spreader 505 is omitted and the heat exchanger 550 is disposed directly over the TEC 110.

Figure 6:
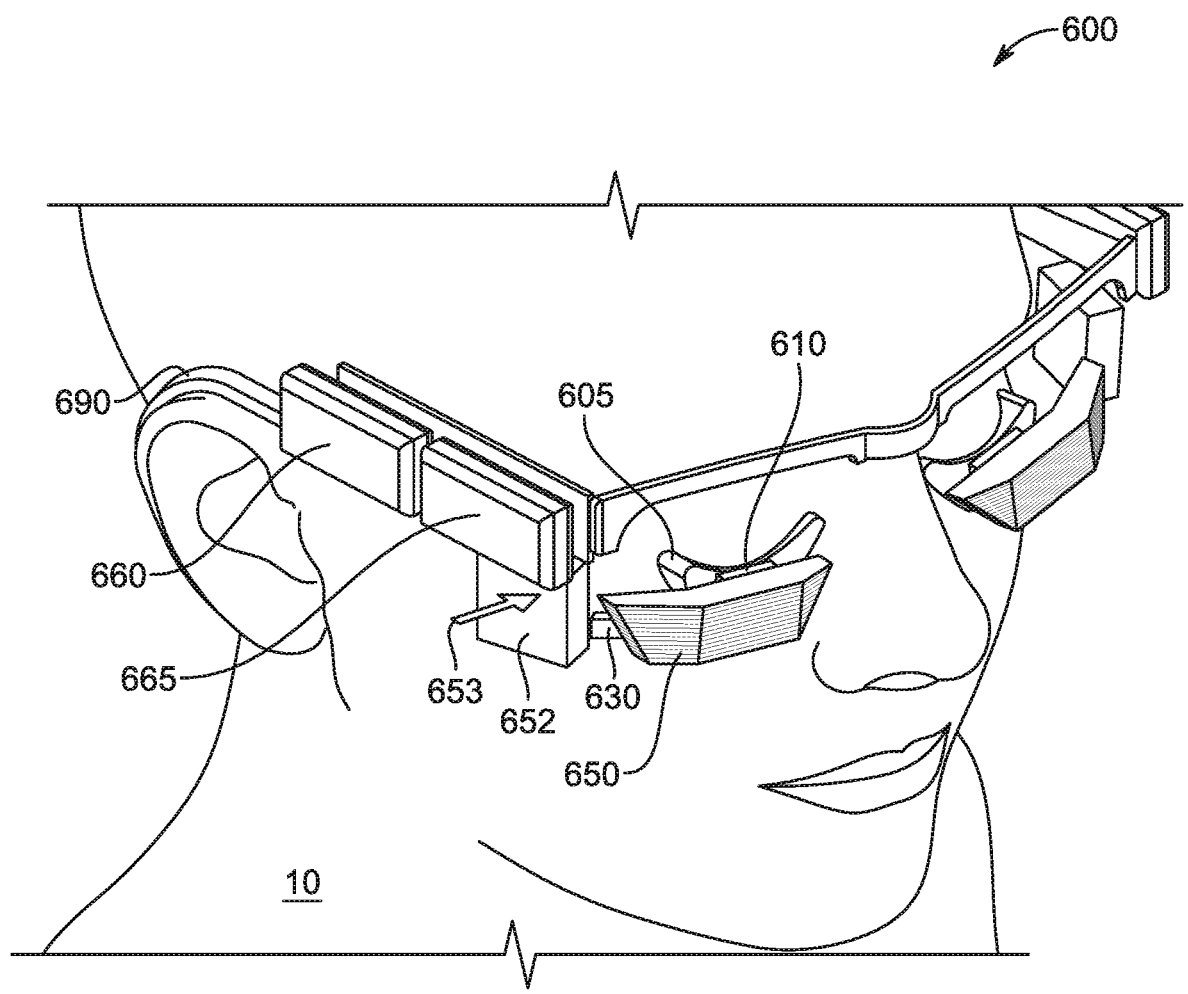
FIG. 6 is a partially schematic isometric view of a heat transfer device being worn by a human, in accordance with embodiments of the present technology.

FIG. 6 is a partially schematic isometric view of a heat transfer device 600 ("device 600") being worn by a human 10, in accordance with embodiments of the present technology. The device 600 can correspond to the device 500 in that the components described with reference to FIG. 5 are all included in the device 600. As shown in FIG. 6, the device 600 includes a frame 690 worn by the human 10, and additional components mechanically coupled to the frame 690 and configured to thermally treat the left and right ocular regions of the human 10. The device 600 includes a contact member 605 (e.g., the contact member 105 (FIG. 1A)) coupled to the frame 690, a TEC 610 (e.g., the TEC 110 (FIG. 1A) or the TEC 410 (FIG. 4)) thermally coupled to the contact member 605, a heat exchanger 650 (e.g., the heat exchanger 150 (FIG. 1A) or the heat exchanger 550 (FIG. 5)) over and configured to remove heat from the TEC 610, a fan 652 fluidically coupled to the heat exchanger 650 via conduit 630, a controller 660 (e.g., the controller 160), and a power source 665 (e.g., the power source 165; FIG. 1A). The conduit 630 can mechanically couple the heat exchanger 650, the TEC 610, and contact member 605 indirectly to the frame 690. As indicated by arrow 653, the conduit 630 is configured to direct cooling fluid from the fan 652 to the heat exchanger 650. In some embodiments, the fan 652 directs air away from the heat exchanger 650 to the ambient environment and thereby pulls heat from the heat exchanger 650. The heat exchanger 650, conduit 630, and fan 652 together can comprise a heat transfer system configured to remove and/or distribute heat from the TEC 110.

In some embodiments, the heat exchanger 650 is mechanically coupled to the frame 690, e.g., via a separate mechanical coupler (not shown), such that the heat exchanger 650, the TEC 610, and/or the contact member 605 are movable relative to the frame 690. The contact member 605 is coupled to the frame 690 such that the contact member 605 contacts a target area (e.g., the under-eye area) of the human 10. The contact member 605 can be pivotably coupled to the TEC 610 and/or the heat exchanger 650, such that the human 10 can adjust the position of the contact member 605 independent of the rest of the device 600. In doing so, the human 10 is able to position the contact member 605 proximate the tissue to be thermally treated, while also not disturbing the fit or comfort of the frame 690.

In operation, the controller 660 receives an input for a desired temperature (e.g., −20° C., −15° C., −10° C., −5° C., 0° C., 5° C., 10° C., or 15° C.) for the cold face of the TEC 610 (i.e., the side of the TEC 610 coupled to the contact member 605), and instructs the power source 665 to deliver a corresponding current to the TEC 610 to enable the desired temperature. As the cold face of the TEC 610 cools to the desired temperature, the hot face (i.e., the opposing side) of the TEC 610 heats up. The heat exchanger 650 removes heat from the hot face of the TEC 610, e.g., via conduction, and is cooled via the fan 652. The fan 652 supplies cooling fluid that absorbs heat from the heat exchanger 650 and is emitted to the ambient environment. The cooling fluid enables the cold face of the TEC 610 to remain at the desired temperature and cool the target area of the facial and ocular region for a desired duration (e.g., at least 10 minutes, 20 minutes, 30 minutes, 45 minutes, 60 minutes, 2 hours, 5 hours, or 10 hours) such that the underlying conditions can be properly treated.

Figure 7:
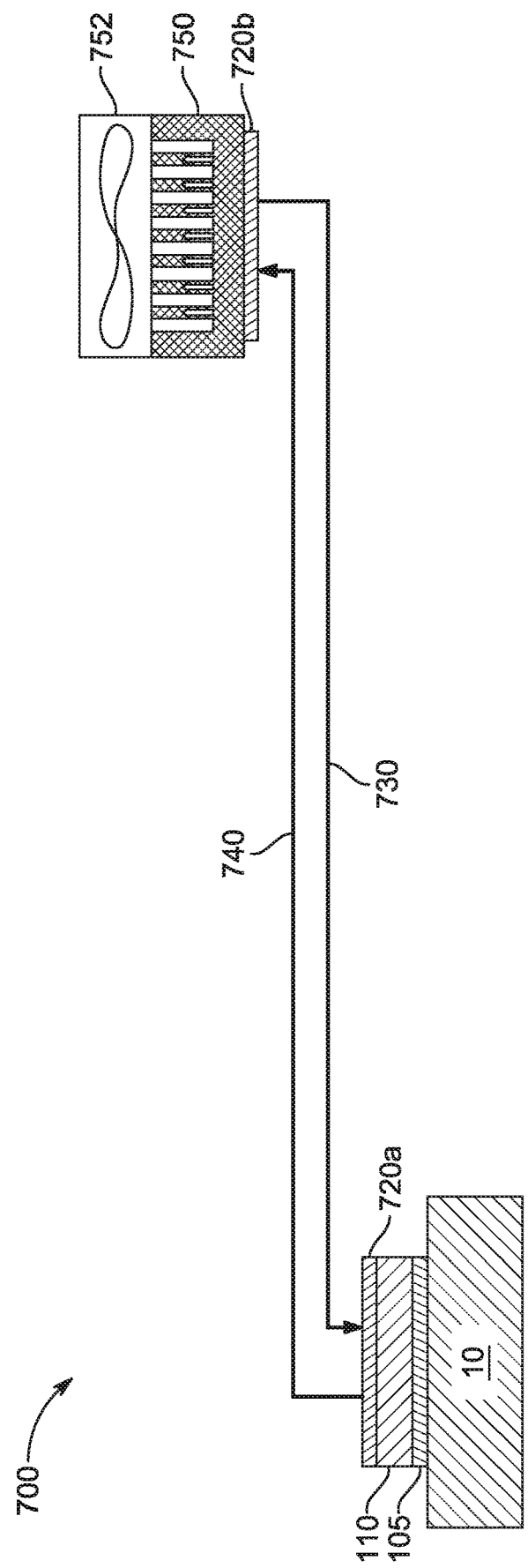
FIG. 7 is a partially schematic side view of a heat transfer device, in accordance with embodiments of the present technology.

FIG. 7 is a partially schematic cross-sectional view of a heat transfer device 700 ("device 700"), in accordance with embodiments of the present technology. The device 700 includes the contact member 105 over the human 10, and the TEC 110 over the contact member 105 and thermally coupled to the human 10, as previously described. The device 700 also includes a heat transfer system thermally coupled to and configured to remove heat from the TEC 110. The heat transfer system includes a first heat transfer structure 720a over and thermally coupled to the TEC 110, a second heat transfer structure 720b, a cold fluid passage 730 (e.g., the cold fluid passage 130 (FIG. 1A)) extending between the first heat transfer structure 720a and the second heat transfer structure 720b, a hot fluid passage 740 (e.g., the hot fluid passage 140 (FIG. 1A)) extending between the first heat transfer structure 720a and the second heat transfer structure 720b, a heat exchanger 750 (e.g., the heat exchanger 550 (FIG. 5)), and a fan 752 (e.g., the fan 552 (FIG. 5)) over the heat exchanger and configured to supply cooling fluid that absorbs heat from the heat exchanger 650. The cold fluid passage 730 is configured to provide a cooled working fluid from the second heat transfer structure 720b to the first heat transfer structure 720a, and the hot fluid passage 740 is configured to provide a heated working fluid from the first heat transfer structure 720a to the second heat transfer structure 720b.

In operation, the cooled working fluid is provided from the second heat transfer structure 720b to the first heat transfer structure 720a and absorbs heat generated from the TEC 110. The resulting heated working fluid is provided via the hot fluid passage 740 to the second heat transfer structure 720b and is cooled via the heat exchanger 750. The fan 752 blows air away from the heat exchanger 750, thereby pulling heat from the heat exchanger 750. The cooled working fluid is provided back to the first heat transfer structure 720a as part of a closed loop heat transfer system that enables the TEC 110 to continue cooling the contact member 105 and/or the human 10 to a desired temperature for a desired duration.

The first heat transfer structure 720a and the second heat transfer structure 720b (collectively referred to as "the heat transfer structures 720a/b") can be similar or identical to the heat transfer structure 220 (FIGS. 2A and 2B). For example, the heat transfer structures 720a/b can each include the chamber 220, the base substrate or member 222 within the chamber 220, the microfeatures 224 (e.g., defined by elongate walls or pillars) that protrude from the base member 222, and the channels 226 formed between and defined by adjacent ones of the microfeatures 224, as previously described with reference to FIGS. 2A and 2B. In such embodiments, for the first heat transfer structure 720a, the cooled working fluid can flow through the channels, absorbing heat from the microfeatures, and indirectly from the TEC, to become the heated working fluid that is then directed to the hot fluid passage 740. For the second heat transfer structure 720b, the heated working fluid can flow through the channels, emitting heat to the microfeatures to become the cooled working fluid that is then directed to the cold fluid passage 730. In some embodiments, the heat transfer structures 720a/b do not correspond to the heat transfer structure 220, and instead include other means for absorbing and/or emitting heat from and/or to the working fluid. For example, the heat transfer structures 720a/b may be containers or heat exchangers without microfeatures.

As indicated in FIG. 7, the first heat transfer structure 720a and the second heat transfer structure 720b can be spaced apart from one another via the cold fluid passage 730 and/or the hot fluid passage 740. In some embodiments, the cold fluid passage 730 and the hot fluid passage 740 can be insulated to prevent exposure of the cold fluid passage 730 and the hot fluid passage 740, which could be respectively cold and hot to the touch. Additionally, the cold fluid passage 740 may be insulated to prevent heat loss of the cooled working fluid contained therein. In some embodiments, the hot fluid passage 740 is not insulated and can comprise a conductive metal (e.g., copper or aluminum) able to radiate heat and promote heat loss. Additionally or alternatively, the length of the hot fluid passage 740 can be longer than the cold fluid passage 730 or maximized to promote heat loss from the heated working fluid to the hot fluid passage 740 and the ambient environment. Advantageously, spacing the heat exchanger 750 apart from the TEC 110 and target area of the human 10 can enable the heat exchanger 750 to have a larger footprint and thereby have a higher heat transfer/removal capacity. If the heat exchanger 750 was disposed over the TEC 110 and/or target area, where space is limited, the heat exchanger 750 may necessarily be smaller so that the device 700 could be comfortably worn by the human 10.

The heat transfer system of the device 700 can be a two-phase or single-phase heat transfer system. When operating as a two-phase heat transfer system, the cooled working fluid is provided to the first heat transfer structure 720a as a liquid, and is heated via heat absorbed from the TEC 110 to become a vapor working fluid. The vapor working fluid travels via the heated working fluid passage 740 to the second heat transfer structure 720b where it is cooled and condensed to become a liquid. When operating as a two-phase heat transfer structure, the first heat transfer structure 720a can be positioned beneath or at a lower elevation than the second heat transfer structure 720b, e.g., to provide additional head pressure from the cooled, liquid working fluid traveling via the cold fluid passage 730 and facilitate flow of the heated, vapor working fluid via the hot fluid passage 740.

Figure 8:
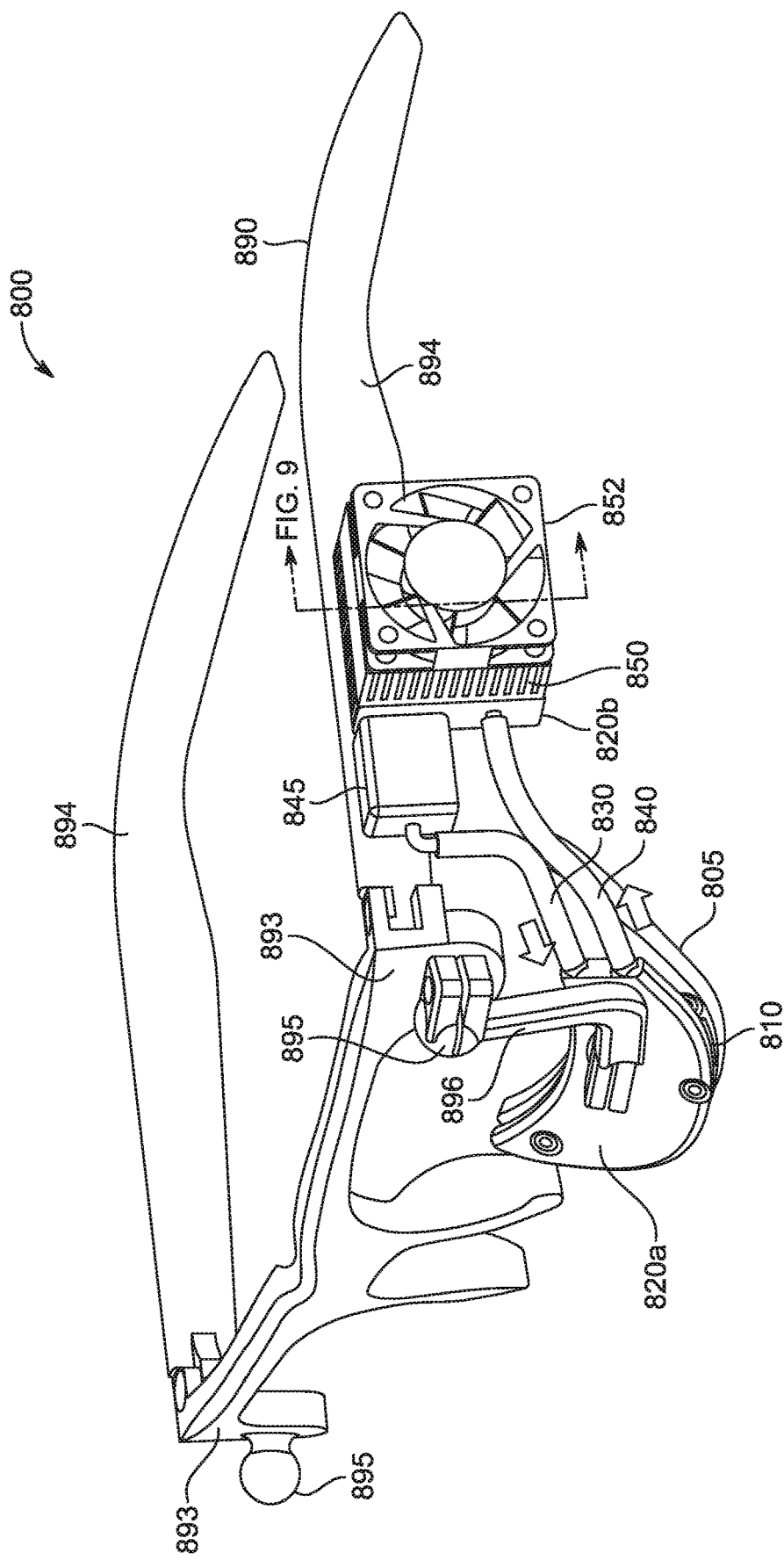
FIG. 8 is a partially schematic isometric view of a heat transfer device configured to be worn by a human, in accordance with embodiments of the present technology.

FIG. 8 is a partially schematic view of a heat transfer device 800 ("device 800") configured to be worn by a human, in accordance with embodiments of the present technology. The device 800 generally corresponds to the device 700 (FIG. 7) in that all of the components of the device 700 are included in the device 800. As shown in FIG. 8, the device 800 includes a frame 890 worn by the human 10, and additional components mechanically coupled to the frame 890 and configured to thermally treat the left and right ocular regions of the human 10. The frame 890 includes end portions 893, a bridge portion 891 extending between the end portions 893, nose portions 892, and temple portions 894 extending from respective ones of the end portions 893. As shown in FIG. 8, the frame 890 can also include couplers 895 and coupling members 896 configured to attach one or more of the components of the device 800 to the frame 890.

The device 800 includes a contact member 805 (e.g., the contact member 105 (FIG. 1A)), a TEC 810 (e.g., the TEC 110 (FIG. 1A) or the TEC 410 (FIG. 4)) thermally coupled to the contact member 805, a first heat transfer structure 820a (e.g., the first heat transfer structure 720a (FIG. 7) or the heat transfer structure 220 (FIGS. 2A and 2B)) thermally coupled to the TEC 810. The first heat transfer structure 820a is pivotably coupled to the frame 890 via the coupler 895 and coupling member 896, such that the first heat transfer structure 820a, the TEC 810, and/or the contact member 805 are independently movable relative to the frame 890 (e.g., the bridge portion 891 or the end portions 893). The device 800 further includes a second heat transfer structure 820b (e.g., the second heat transfer structure 720b (FIG. 7) or the heat transfer structure 220 (FIGS. 2A and 2B)), a cold fluid passage 830 (e.g., the cold fluid passage 730 (FIG. 7) or the cold fluid passage 230 (FIGS. 2A and 2B)) fluidically coupling the second heat transfer structure 820b to the first heat transfer structure 820a, a hot fluid passage 840 (e.g., the hot fluid passage 740 (FIG. 7) or the hot fluid passage 240 (FIGS. 2A and 2B)) fluidically coupling the second heat transfer structure 820b to the first heat transfer structure 820a, a heat exchanger 850 (e.g., the heat exchanger 750 (FIG. 7)), and a fan 852 (e.g., the fan 752 (FIG. 7)). The first heat transfer structure 820a, the second heat transfer structure 820b, the cold fluid passage 830, the hot fluid passage 840, the heat exchanger 850, and the fan 852 can together comprise a heat transfer system configured to remove and/or distribute heat from the TEC 110. The first heat transfer structure 820a can be positioned beneath or at a lower elevation than the second heat transfer structure 820b, e.g., to provide additional head pressure from the cooled, liquid working fluid traveling via the cold fluid passage 830, and, when operating as a two-phase heat transfer system, to facilitate flow of the heated, vapor working fluid via the hot fluid passage 840.

As shown in FIG. 8, the device 800 also includes a pump 845 fluidically coupled to the second heat transfer structure 820b and the cold fluid passage 830. In some embodiments the pump 845 is mechanically coupled to the frame 890, or more specifically to the temple 894. The pump 845 increases the pressure of the cooled working fluid, enabling more effective heat transfer from the TEC 810 to the first heat transfer structure 820a and ensuring adequate working fluid flow throughout the closed-loop system to adequately cool the TEC 810. In some embodiments, the pump 845 is omitted.

In operation, a controller (e.g., the controller 160 (FIG. 1)) receives an input for a desired temperature (e.g., −20° C., −15° C., −10° C., −5° C., 0° C., 5° C., 10° C., or 15° C.) for the cold face of the TEC 810 (i.e., the side of the TEC 810 coupled to the contact member 805), and instructs a power source (e.g., the power source 165 (FIG. 1A)) to deliver a corresponding current to the TEC 810 to enable the desired temperature. As the cold face of the TEC 810 cools to the desired temperature, so does the contact member 805 and the target area of the human 10. Additionally, as the cold face of the TEC 810 cools, the hot face (i.e., the opposing side) of the TEC 810 heats up. The cooled working fluid passing through the first heat transfer structure 820a absorbs heat from the TEC 810 to become heated working fluid that is directed to the second heat transfer structure 820b to be cooled. The heat exchanger 850 removes heat from the heated working fluid, e.g., via conduction, and is cooled via the fan 832. The fan 832 supplies cooling fluid that absorbs heat from the heat exchanger 850 and is emitted to the ambient environment. Such cooling enables the cold face of the TEC 810 to remain at the desired temperature and cool the target area of the facial and ocular region for a desired duration such that the underlying conditions can be properly treated.

Figure 9:
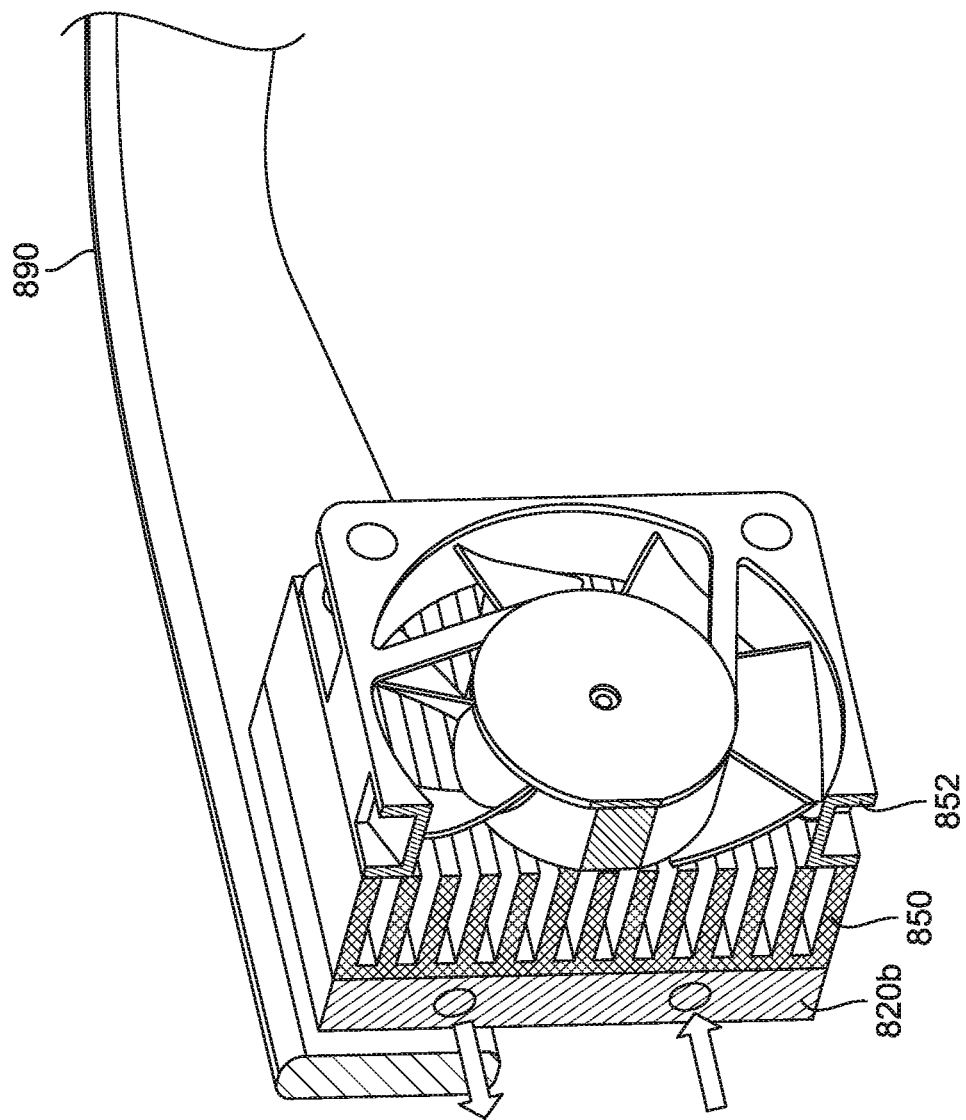
FIG. 9 is an enlarged partially schematic cross-sectional isometric view of a portion of the heat transfer device shown in FIG. 8.

FIG. 9 is an enlarged partially schematic cross-sectional view of a portion of the device 800 of FIG. 8. As shown in FIG. 9, the second heat transfer structure 820b is mechanically coupled to the frame 890, the heat exchanger 850 is mechanically coupled to the second heat transfer structure 820b, and the fan 852 is mechanically coupled to the heat exchanger 850. Advantageously, by coupling the heat exchanger 850 and fan 852 to the temple portion 894 of the frame 890, and away from the TEC 810 and target area being thermally treated, the heat exchanger 850 can have a larger footprint and thereby have a higher heat transfer capacity. If the heat exchanger 850 was disposed over the TEC 810 and/or target area, where space is limited, the heat exchanger 850 may need to be smaller so the device 700 can be comfortably worn by the human 10.

Figure 10:
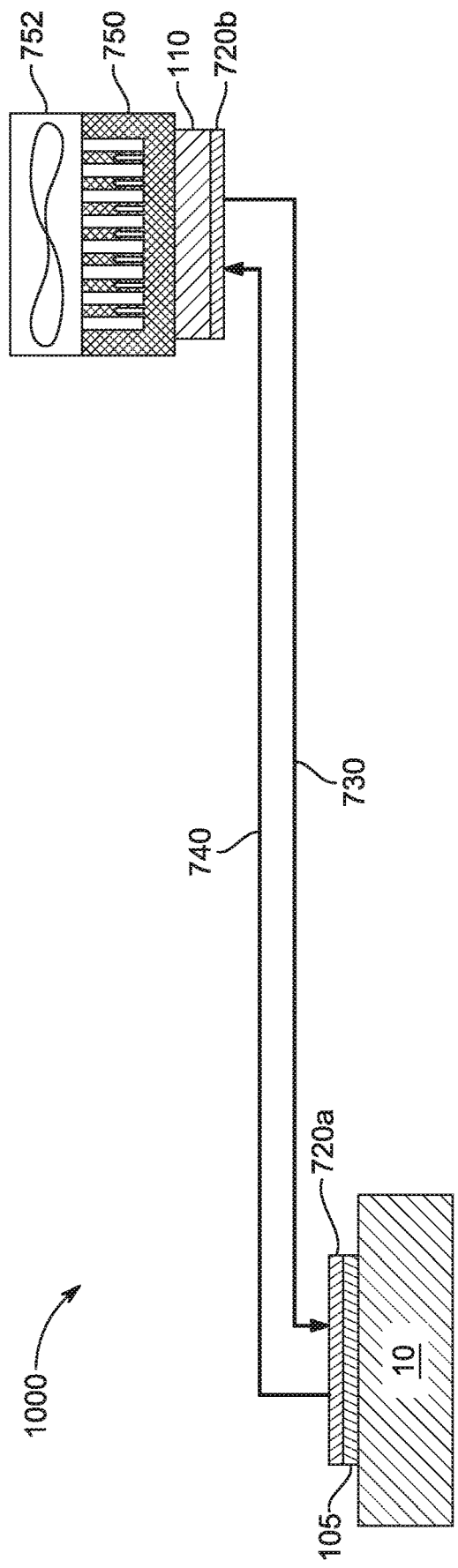
FIG. 10 is a partially schematic side view of a heat transfer device, in accordance with embodiments of the present technology.

FIG. 10 is a partially schematic cross-sectional view of a heat transfer device 1000 ("device 1000"), in accordance with embodiments of the present technology. The device 1000 is similar to the device 800 in that the device 1000 includes the contact member 105, first heat transfer structure 720a, cold fluid passage 730, hot fluid passage 740, second heat transfer structure 720b, TEC 110, heat exchanger 750, and fan 752. However, as shown in FIG. 10, the device 1000 arranges these components differently than that of device 800. Specifically, the TEC 110 is spaced apart from the contact member 105, as opposed to being directly coupled to the contact member 105. In such an arrangement, the device 1000 can achieve a more gradual thermal response at the target area of the human 10 over slightly longer time periods relative to that of the device 800. Additionally or alternatively, the device 1000 can enable the contact member 105 to have more flexibility because it is not restrained by the rigidity of the TEC 110, and result in a thinner structure at the target area. The added flexibility and thinner structure of the device 1000 can allow the device 1000 to better contour and contact the surface of the target area and enable better heat transfer between the device 1000 and target area.

As shown in FIG. 10, the first heat transfer structure 720a is positioned over (e.g., directly over) and thermally coupled to the contact member 105. The first heat transfer structure 720a is fluidically coupled to the second heat transfer structure 720b via the cold fluid passage 730 and the hot fluid passage 740. The TEC 110 is positioned between and thermally coupled to the second heat transfer structure 720b and the heat exchanger 750, with the cold face of the TEC 110 being proximate and/or in contact with the second heat transfer structure 720b and the hot face of the TEC 110 being proximate and/or in contact with the heat exchanger 750. The first heat transfer structure 720a, the second heat transfer structure 720b, the cold fluid passage 730, the hot fluid passage 740, the heat exchanger 750, and the fan 752 can together comprise a heat transfer system configured to remove and/or distribute heat from the contact member 105 and/or TEC 110.

The heat transfer system of the device 1000 can include be a two-phase or single-phase heat transfer system. When operating as a two-phase heat transfer system, the cooled working fluid is provided to the first heat transfer structure 720a as a liquid, and is heated via heat absorbed from the contact member 105 to become a vapor working fluid. The vapor working fluid travels via the heated working fluid passage 740 to the second heat transfer structure 720b where it is cooled via the TEC 110 and condensed to become a liquid. When operating as a two-phase heat transfer structure, the first heat transfer structure 720a can be positioned beneath or at a lower elevation than the second heat transfer structure 720b, e.g., to provide additional head pressure from the cooled, liquid working fluid traveling via the cold fluid passage 730 and facilitate flow of the heated, vapor working fluid via the hot fluid passage 740.

Figure 11:
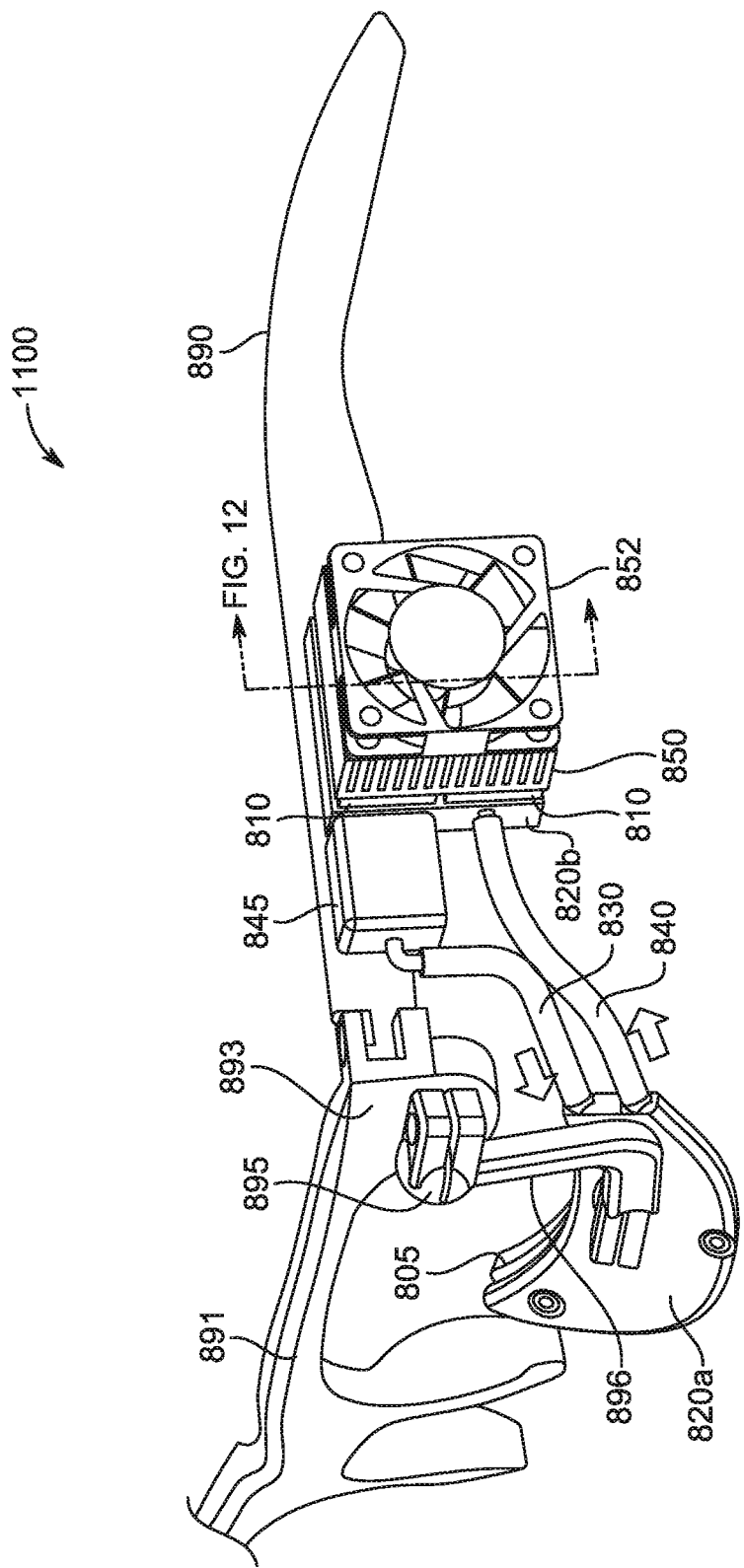
FIG. 11 is a partially schematic isometric view of a heat transfer device configured to be worn by a human, in accordance with embodiments of the present technology.

FIG. 11 is a partially schematic isometric view of a heat transfer device 1100 ("device 1100") configured to be worn by a human, in accordance with embodiments of the present technology. The device 1100 generally corresponds to the device 800 (FIG. 8) and the device 1000 (FIG. 10) in that all of the components of the device 1100 are included in the device 800 and the device 1000. As shown in FIG. 11, the device 1100 includes the frame 890 worn by the human, and additional components mechanically coupled to the frame 890 and configured to thermally treat the left and right ocular regions of the human 10.

The device 1100 includes the contact member 805, and the first heat transfer structure 820a thermally coupled to the contact member 805. As shown in FIG. 11, the first heat transfer structure 820a and the contact member 805 can have the same or similar shape, which maximizes surface area contact for more effective heat transfer. The first heat transfer structure 820a is pivotably coupled to the frame 890 via the coupler 895 and coupling member 896, such that the first heat transfer structure 820a and/or the contact member 805 are independently movable relative to the frame 890 (e.g., the bridge portion 891 or the end portions 893). The device 1100 further includes the second heat transfer structure 820b, the cold fluid passage 830 fluidically coupling the second heat transfer structure 820b to the first heat transfer structure 820a, the hot fluid passage 860 fluidically coupling the second heat transfer structure 820b to the first heat transfer structure 820a, the heat exchanger 850, the TEC 810 between and thermally coupled to the heat exchanger 850 and the second heat transfer structure 820b, and the fan 852 over the heat exchanger 850. As shown in FIG. 11, the second heat transfer structure 820b, heat exchanger 850, TEC 810, and fan 852 are coupled to the temple portion 894 and are thus spaced apart from the contact member 1105 and target area being thermally treated. The first heat transfer structure 820a can be positioned beneath or at a lower elevation than the second heat transfer structure 820b, e.g., to provide additional head pressure from the cooled, liquid working fluid traveling via the cold fluid passage 830, and, when operating as a two-phase heat transfer system, to facilitate flow of the heated, vapor working fluid via the hot fluid passage 840.

As shown in FIG. 11, the device 1100 also includes the pump 845 fluidically coupled to the second heat transfer structure 820b and the cold fluid passage 830. In some embodiments the pump 845 is mechanically coupled to the frame 890, or more specifically to the temple 894. The pump 845 increases the pressure of the cooled working fluid, enabling more effective heat transfer from the first heat transfer structure 820a to the contact member 805, and ensuring adequate working fluid flow throughout the closed-loop system to adequately cool the contact member 805. In some embodiments, the pump 845 is omitted.

Figure 12:
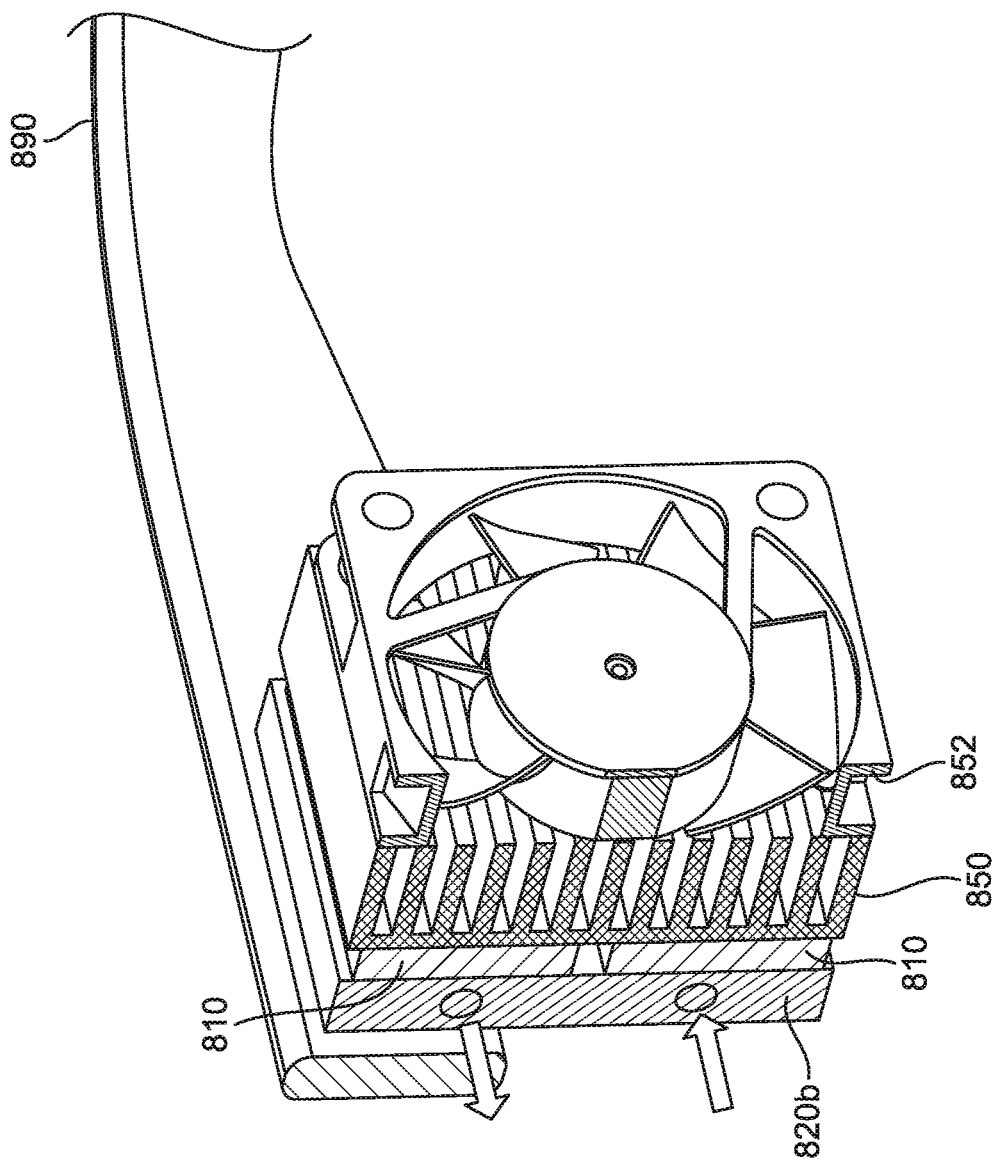
FIG. 12 is an enlarged partially schematic cross-sectional isometric view of a portion of the heat transfer device shown in FIG. 11.

FIG. 12 is an enlarged partially schematic cross-sectional view of a portion of the device 1100 of FIG. 10. As shown in FIG. 12, the second heat transfer structure 820b is mechanically coupled to the frame 890, the TEC 810 is thermally coupled and mechanically coupled to the second heat transfer structure 820b, the heat exchanger 850 is mechanically coupled to the TEC 810, and the fan 852 is mechanically coupled to the heat exchanger 850. Advantageously, by coupling the heat exchanger 850 and fan 852, in addition to the second heat transfer structure 820b and TECs 810, to the temple portion 894 of the frame 890, and away from the contact member 805 and target area being thermally treated, the heat exchanger 850 and fan 852, for example, can have a larger footprint and thereby have a higher heat transfer capacity. If the heat exchanger 850 and/or fan 852 were disposed over the contact member 805 and/or target area, where space is limited, the heat exchanger 850 and/or fan 852 may need to be smaller so the device 1100 can be comfortably worn by the human.

FIG. 13A is a partially schematic cross-sectional view of a heat transfer device 1300 ("device 1300"), in accordance with embodiments, of the present technology. The device 1300 is similar to the device 800 in that the device 1300 includes the contact member 105, TEC 110, heat exchanger 750, and fan 752. As shown in FIG. 13, the device 1300 further includes a thermal strap or interfacial material 1305 ("thermal strap 1305") (e.g., the heat spreader 505 (FIG. 5)), and a heat transfer structure 1330 extending from the TEC 110 to the thermal strap 1305. The thermal strap 1305 can be a flexible material adding flexibility to the device 1300 and able to accommodate movement of the heat transfer structure 1320 relative to the heat exchanger 750. Additionally or alternatively, the thermal strap 1305 can be positioned between the contact member 105 and the TEC 110 and/or between the TEC 110 and the evaporator portion of the heat transfer structure 1320. The thermal strap 1305 may comprise copper, aluminum, or other materials with high thermal conductivity. The heat transfer structure 1320, the thermal strap 1305, the heat exchanger 750, and the fan 852 can together comprise a heat transfer system configured to remove and/or distribute heat from the contact member 105 and/or TEC 110.

The heat transfer structure 1320 can be a heat pipe or an elongate structure that is vacuum sealed. The heat transfer structure 1320 includes an evaporator portion adjacent the TEC 110 at a proximal region of the heat transfer structure 1320, and a condenser portion adjacent the thermal strap1305 at a distal region of the heat transfer structure 1320. In some embodiments, the device 1300 includes a conductive block between and coupled to the TEC 110 and the evaporation portion of the heat transfer structure 1320. As shown in FIG. 13B, which is a partially schematic cross-sectional view of the heat transfer structure 1320, the heat transfer structure 1320 can include an outer material 1332 (e.g., copper or aluminum), a wicking material 1334 radially inward of and lining the outer material 1332, and a void 1336 radially inward of and enveloped by the wicking material 1334. The void 1336 can contain a working fluid (WF) that transitions between a vapor and liquid as it transitions between the evaporation portion and condenser portion of the heat transfer structure 1320. The wicking material can be grooved, sintered, or comprise a wire mesh. In some embodiments, the device 1300 includes insulation surrounding the heat transfer structure 1320 to prevent exposure of the heat transfer structure 1320, which could be cold or hot to the touch.

In operation, a controller (e.g., the controller 130 (FIG. 1)) receives an input for a desired temperature (e.g., −20° C., −15° C., −10° C., −5° C., 0° C., 5° C., 10° C., or 15° C.) for the cold face of the TEC 110 (i.e., the side of the TEC 110 coupled to the contact member 105), and instructs a power source (e.g., the power source 165 (FIG. 1A)) to deliver a corresponding current to the TEC 110 to enable the desired temperature. As the cold face of the TEC 110 cools to the desired temperature, so does the contact member 105 and the target area of the human 10. Additionally, as the cold face of the TEC 110 cools, the hot face (i.e., the opposing side) of the TEC 110 heats up, which applies heat to the evaporation portion of the heat transfer structure 1320. As heat from the TEC 110 is applied to the heat transfer structure 1320 at the evaporation portion, the working fluid within the heat transfer structure 1320 is heated and changes into a vapor working fluid, which is facilitated by the sealed vacuum of the heat transfer structure 1320. The vapor working fluid causes the pressure to increase within the heat transfer structure 1320, which causes the vapor working fluid to flow toward the cooler side or condenser portion of the heat transfer structure 1320. At the condenser portion the heat of the vapor working fluid is released and the vapor working fluid condenses to a liquid working fluid. The condensed liquid working fluid then flows back toward the hotter side or evaporator portion, where the cycle repeats as long as heat continues to be applied via the TEC 110. The thermal strap1305 absorbs heat from the heat transfer structure 1320, and the heat exchanger 750 removes heat from the thermal strap1305, e.g., via conduction. The heat exchanger 750 is cooled via the fan 752, which supplies cooling fluid that absorbs heat from the heat exchanger 750 and is emitted to the ambient environment. Such cooling enables the cold face of the TEC 110 to remain at the desired temperature and cool the target area (e.g., of the facial and ocular region) for a desired duration such that the underlying conditions can be properly treated.

Figure 14A:
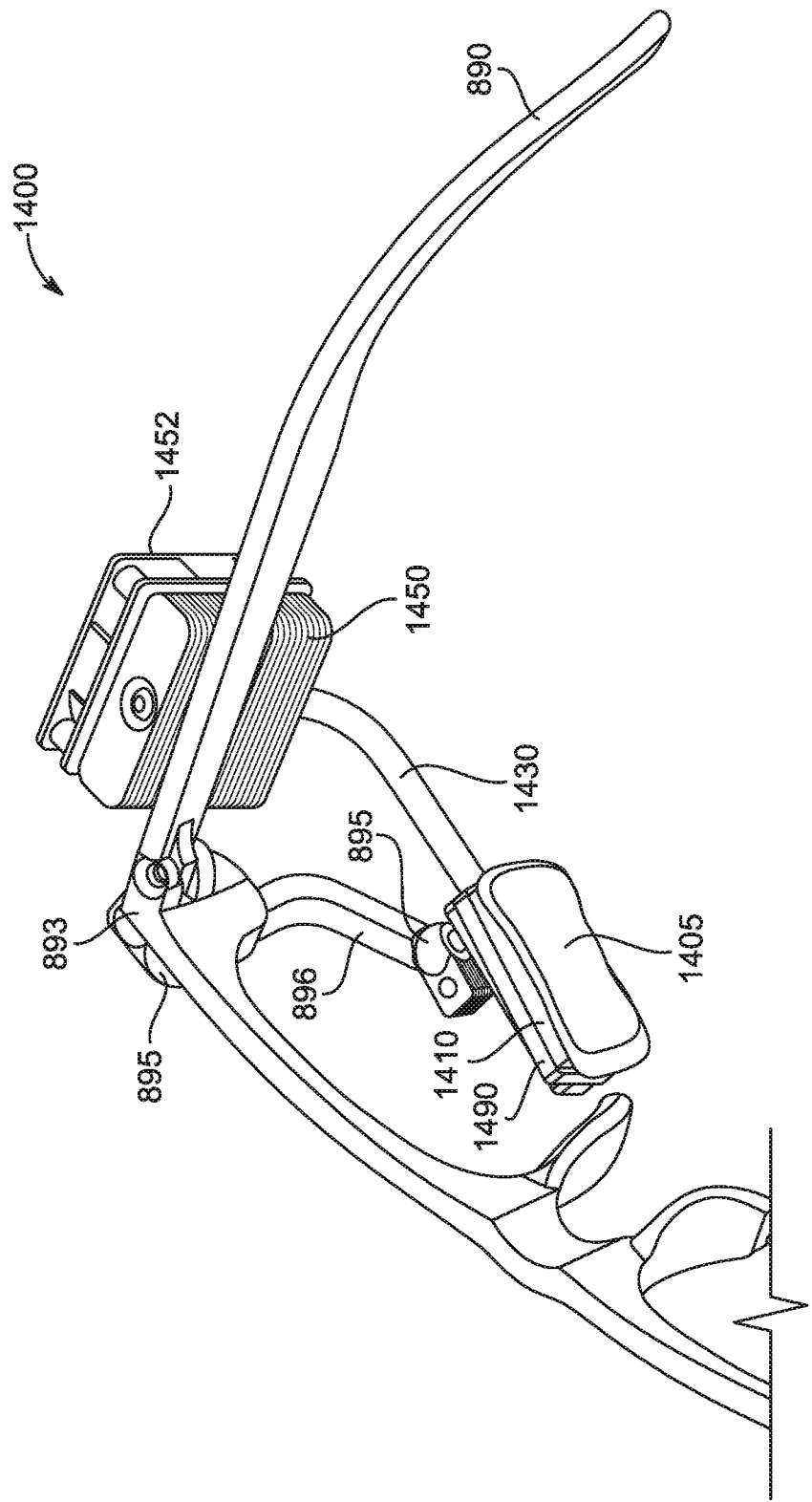
FIGS. 14A and 14B are partially schematic isometric views of a heat transfer device configured to be worn by a human, in accordance with embodiments of the present technology.
Figure 14B:
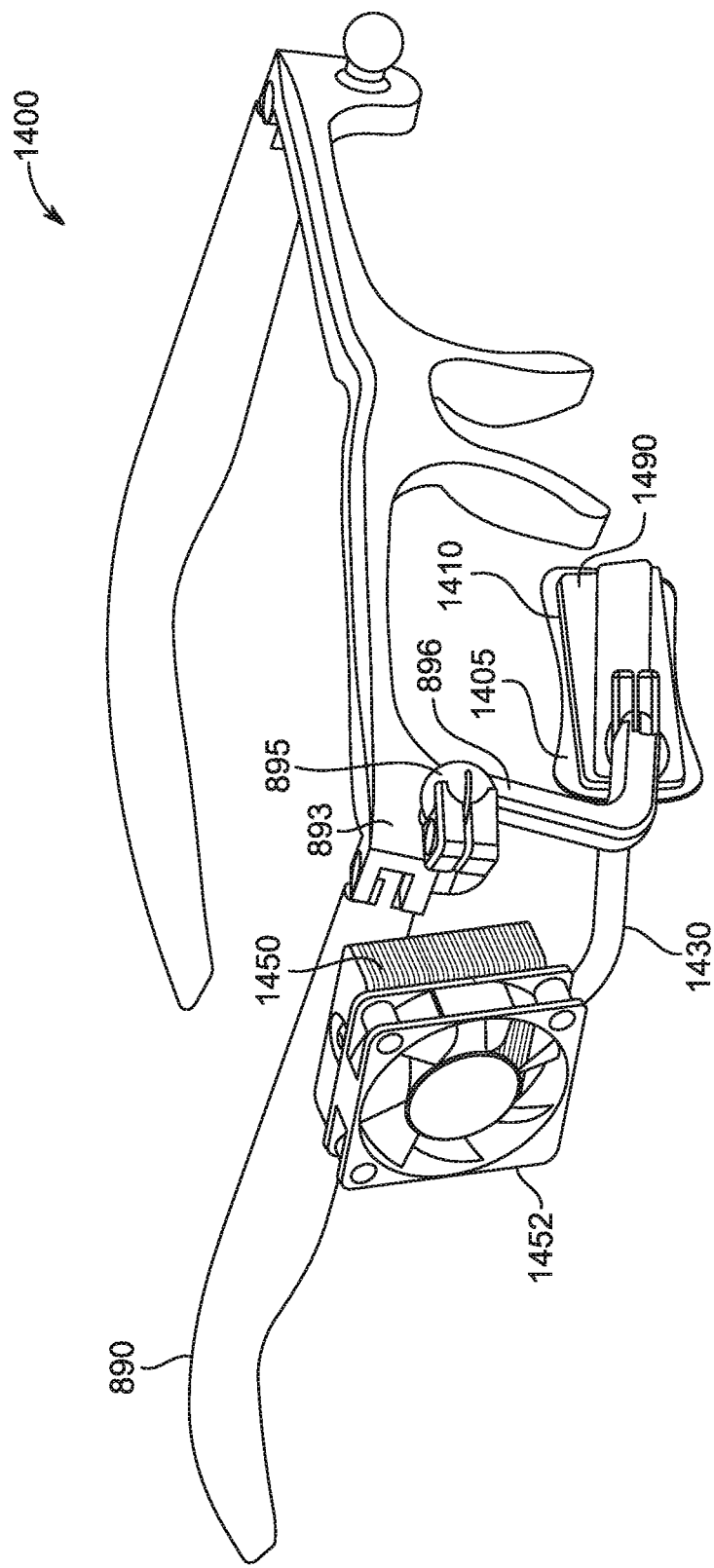

FIGS. 14A and 14B are partially schematic views of a heat transfer device 1400 ("device 1400") configured to be worn by a human, in accordance with embodiments of the present technology. The device 1400 generally corresponds to the device 1300 (FIG. 13) being incorporated onto a frame 1490. Referring to FIGS. 14A and 14B together, the device 1400 includes the frame 890 previously described with reference to FIG. 8, and additional components mechanically coupled to the frame 890 and configured to thermally treat the left and right ocular regions of the human 10.

The device 1400 includes a contact member 1405 (e.g., the contact member 805 (FIG. 8)), a TEC 1410 (e.g., the TEC 810 (FIG. 8)) thermally coupled to the contact member 1405, a conductive block 1490 thermally coupled to the TEC 1410, and a heat pipe 1430 (e.g., the heat transfer structure 1320 (FIG. 13)) thermally coupled to the conductive block 1490 and/or TEC 1410. The heat pipe 1430, conductive block 1490, and/or the TEC 1410 can be pivotably coupled to the frame 890 via the coupler 895 and coupling member 896, such that the heat pipe 1430, conductive block 1490, TEC 1410, and/or contact member 1405 are independently movable relative to the frame 890 (e.g., the bridge portion 891 or the end portions 893). The device 1400 further includes a heat exchanger 1450 (e.g., the heat exchanger 850 (FIG. 8)) coupled to an end portion of the heat pipe 1430, and a fan 1452 (e.g., the fan 852 (FIG. 8)).

In operation, a controller (e.g., the controller 130 (FIG. 1)) receives an input for a desired temperature (e.g., −20° C., −15° C., −10° C., −5° C., 0° C., 5° C., 10° C., or 15° C.) for the cold face of the TEC 1410 (i.e., the side of the TEC 1410 coupled to the contact member 1405), and instructs a power source (e.g., the power source 165 (FIG. 1A)) to deliver a corresponding current to the TEC 1410 to enable the desired temperature. As the cold face of the TEC 1410 cools to the desired temperature, so does the contact member 805 and the target area of the human 10. Additionally, as the cold face of the TEC 810 cools, the hot face (i.e., the opposing side) of the TEC 810 heats up and applies heat to the evaporation portion of the heat pipe 1430. Subsequently, working fluid within the heat pipe 1430 is vaporized, which causes the pressure to increase within the heat transfer structure 1320 and the vapor working fluid to flow toward the condenser portion of the heat pipe 1430. The heat exchanger 1450 removes heat from the condenser portion of the heat pipe 1430, e.g., via conduction, and the heat exchanger 1450 is cooled via the fan 1452.

Figure 15:
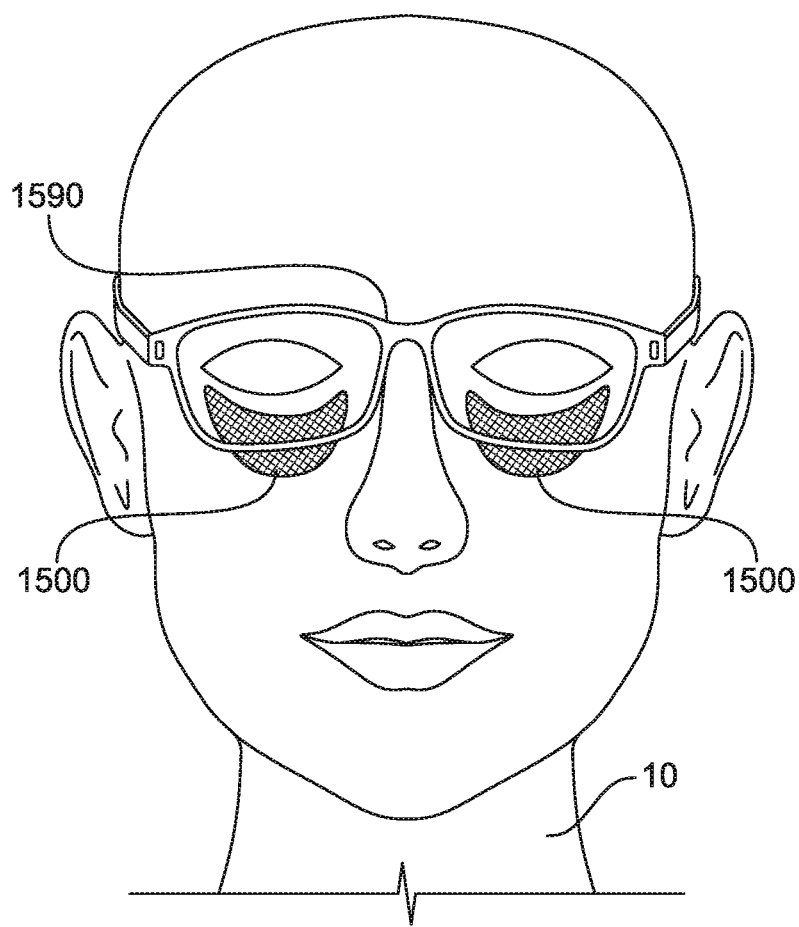
FIG. 15 is a partially schematic front view of a heat transfer device being worn by a human, in accordance with embodiments of the present technology.
Figure 16:
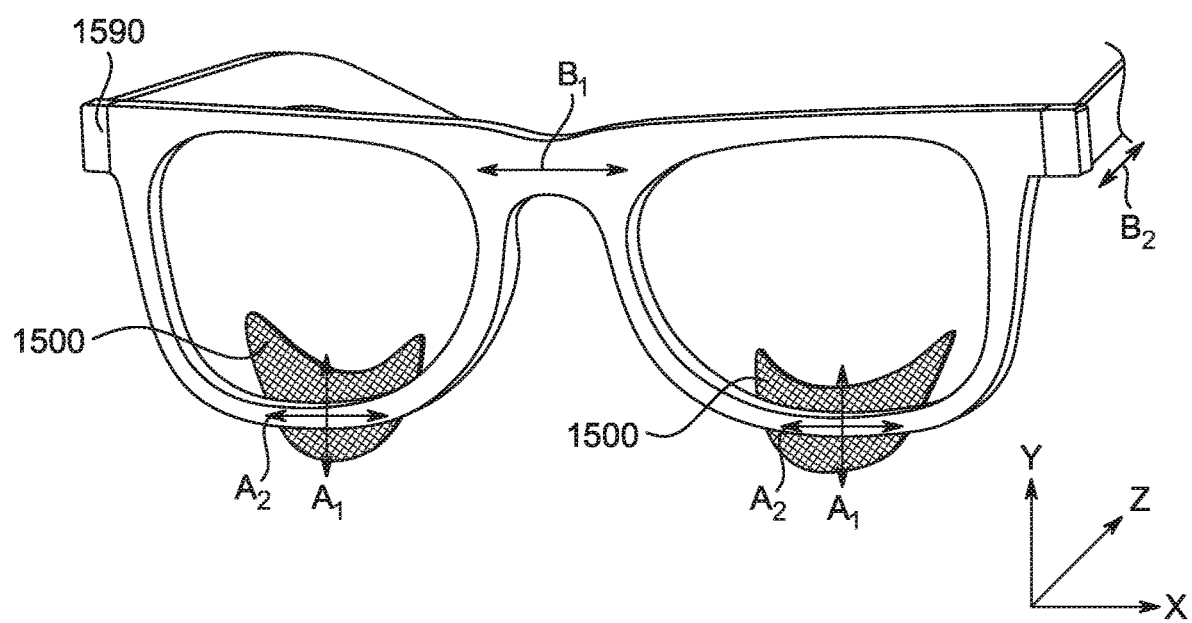
FIG. 16 is a partially schematic isometric view of the ocular device shown in FIG. 15.

FIG. 15 is a partially schematic front view of a heat transfer device 1500 ("device 1500") coupled to an ocular frame 1590 worn by a human 10, and FIG. 16 is an isometric view of the device 1500 and frame 1590, in accordance with embodiments of the present technology. The device 1500 can correspond to any of the heat transfer devices described herein, including devices 100, 200, 700, 1000, 1300, and the frame 1590 can correspond to any of the frames described herein, including frame 890.

The device 1500 can be placed at the target ocular area of the human 10 using any fastener, adhesive, strap, tape (e.g., Velcro), belt, or other know means. However, since the under eye skin is relatively sensitive and thin, using any fastener that applies pressure (e.g., vacuum, straps, Velcro, etc.) may cause damage to the skin or tissue. Also, the device 1500 can be displaced with minor motion of the head, and it may not be practical for humans to refrain from moving during thermal treatment. Accordingly, as shown FIGS. 15 and 16, the device 1500 may be disposed against the target ocular area using the frame 1590 that the device 1500 is coupled to. The device 1500 can be configured to improve the thermal contact with the target ocular area. When the frame 1590 is worn by the human 10, the device 1500 is placed in contact with the human 10 at the target area. In doing so, the device 1500 can be held in place to enable therapy while the human 10 has the freedom the move his or her head with limited risk of the device 1500 being displaced.

As shown in FIG. 16, the frame 1590 can be adjusted to accommodate different humans 10 and allow for better thermal contact with the device 1500. For example, the frame 1590 of the device 1500 can be adjusted along the x-axis as illustrated by $B_1$ and/or along the y-axis as illustrated by $B_2$, as well as along the y-axis as illustrated by $A_1$, and/or along the x-axis as illustrated by $A_2$. In doing so, the frame 1590 can be placed to enable optimal thermal contact with the target ocular area.

Figure 17:
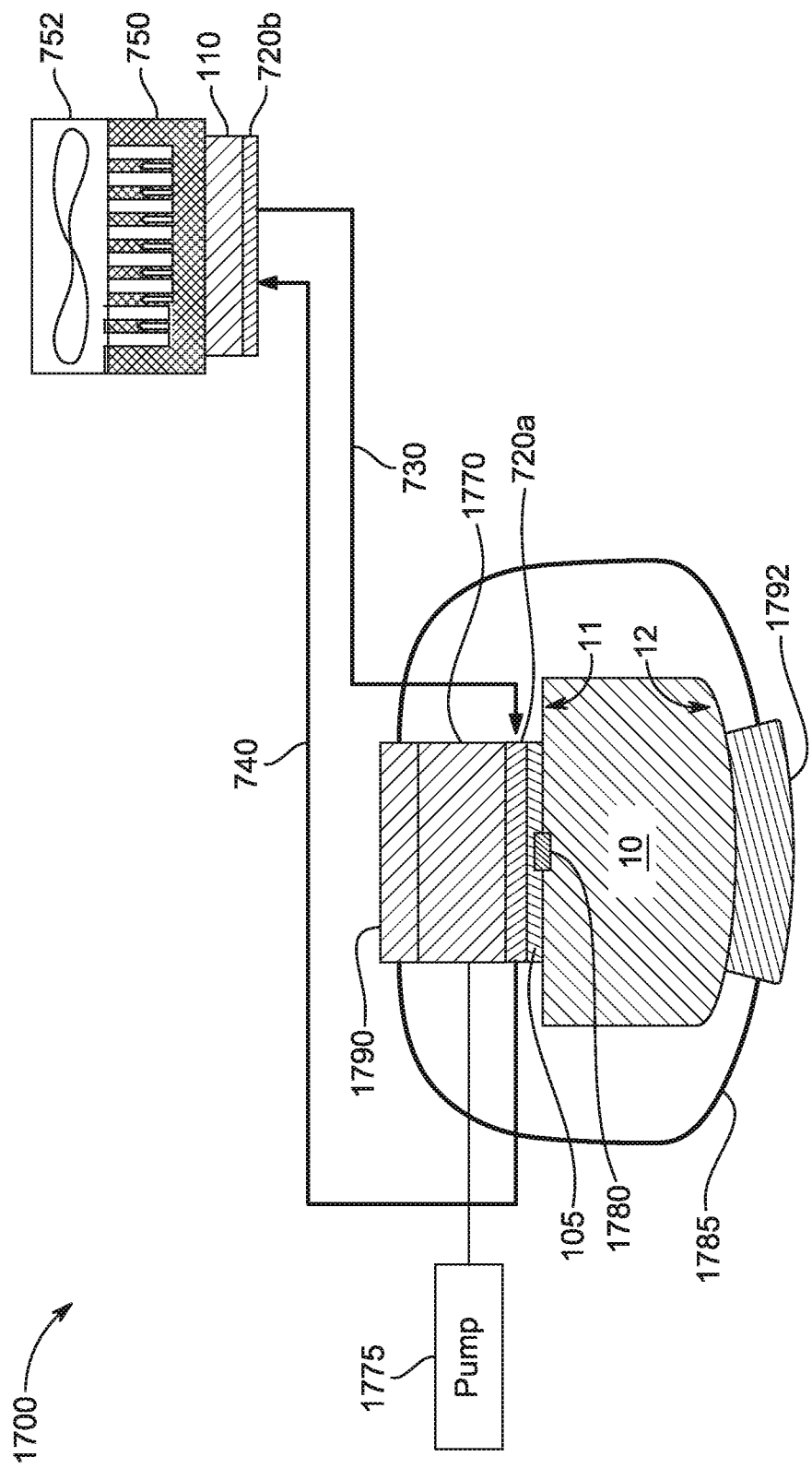
FIG. 17 is a partially schematic cross-sectional top view of a heat transfer device, in accordance with embodiments of the present technology.

FIG. 17 is a partially schematic cross-sectional view of a heat transfer device 1700 ("device 1700"), in accordance with embodiments of the present technology. The device 1700 is similar to the device 1000 in that the device 1700 includes the contact member 105, first heat transfer structure 720a, cold fluid passage 730, hot fluid passage 740, second heat transfer structure 720b, TEC 110, heat exchanger 750, and fan 752. As shown in FIG. 17, the first heat transfer structure 720a is positioned over (e.g., directly over) and thermally coupled to the contact member 105. The first heat transfer structure 720a is fluidically coupled to the second heat transfer structure 720b via the cold fluid passage 730 and the hot fluid passage 740. The TEC 110 is positioned between and thermally coupled to the second heat transfer structure 720b and the heat exchanger 750, with the cold face of the TEC 110 being proximate and/or in contact with the second heat transfer structure 720b and the hot face of the TEC 110 being proximate and/or in contact with the heat exchanger 750. The heat exchanger 750 removes heat from the TEC 110, e.g., via conduction, and is cooled via the fan 752, which supplies cooling fluid that absorbs heat from the heat exchanger 750 and is emitted to the ambient environment. The first heat transfer structure 720a, the second heat transfer structure 720b, the cold fluid passage 730, the hot fluid passage 740, the heat exchanger 750, and the fan 752 can together comprise a heat transfer system configured to remove and/or distribute heat from the contact member 105 and/or TEC 110.

The device 1700 further includes an inflatable interface 1770 over the first heat transfer structure 720a and the contact member 105, and a pump 1775 fluidically coupled to the inflatable interface 1770 and configured to inflate and/or deflate the inflatable interface 1770. The device 1700 further includes a rigid frame 1790 over the inflatable interface 1770 on a first side 11 of the human 10, a rigid member 1792 disposed on a second, opposing side 12 of the human 10, and an adjustable band extending between the rigid frame 1790 and the rigid member 1792 and configured to secure the device 1700 to the human 10. When the device 1700 is worn by the human 10, the rigid frame 1790 applies pressure on and pushes the contact member 105 toward the first side 11 of the human 10. As the inflatable interface 1770 is inflated via the pump 1775, more pressure is applied to the first heat transfer structure 720a and contact member 105, which improves contact and/or heat transfer from the contact member 105 to the human 10.

The device 1700 can further include the user interface 170, the controller 160 operably coupled to the user interface 170, and the power source 165 operably coupled to the controller 160 and the pump 1775, as previously described herein (e.g., with reference to FIG. 1A). The user interface 170, controller 160, and/or power source 165 can be located and/or contained within the rigid member 1792. The device can further include a pressure sensor 1780 operably coupled to the controller 1770 and positioned at the interface between the contact member 105 and the human 10. The pressure sensor 1780 can detect a contact pressure of the device 1700 or contact member 105 applied against the human 10, and can be used as an input for adjusting the inflatable interface 1770. For example, the pump 1775 can be configured to inflate and/or deflate the inflatable interface 1770 based on a signal from the pressure sensor 1780, e.g., to maintain a set contact pressure or to adjust the pressure between various pressures to induce a massage sensation during thermal treatment.

The heat transfer system of the device 1700 can be a two-phase or single-phase heat transfer system. When operating as a two-phase heat transfer system, the cooled working fluid is provided to the first heat transfer structure 720a as a liquid, and is heated via heat absorbed from the contact member 105 to become a vapor working fluid. The vapor working fluid travels via the heated working fluid passage 740 to the second heat transfer structure 720b where it is cooled via the TEC 110 and condensed to become a liquid. When operating as a two-phase heat transfer structure, the first heat transfer structure 720a can be positioned beneath or at a lower elevation than the second heat transfer structure 720b, e.g., to provide additional head pressure from the cooled, liquid working fluid traveling via the cold fluid passage 730 and facilitate flow of the heated, vapor working fluid via the hot fluid passage 740.

In operation, a controller (e.g., the controller 130 (FIG. 1)) receives an input for a desired temperature (e.g., −20° C., −15° C., −10° C., −5° C., 0° C., 5° C., 10° C., or 15° C.) for the cold face of the TEC 110, which is directly correlated to the temperature of the cooled working fluid and/or the temperature of the contact member 105. The controller instructs a power source (e.g., the power source 165 (FIG. 1A)) to deliver a corresponding current to the TEC 110 to enable the desired temperature. As the cold face of the TEC 110 cools to the desired temperature, so does the working fluid being supplied from the second heat transfer structure 720b to the first heat transfer structure 720a, which in turn cools the contact member 105. Additionally, as the cold face of the TEC 110 cools, the hot face (i.e., the opposing side) of the TEC 110 heats up. The heat exchanger 750 removes heat from the TEC 110, e.g., via conduction, and is cooled via the fan 752, which supplies cooling fluid that absorbs heat from the heat exchanger 750 and is emitted to the ambient environment. While this thermal treatment is occurring, the controller can also operate the pump 1775 to inflate the inflatable interface 1770 between the first heat transfer structure 720a and the rigid frame 1790, which can increase the pressure applied by the contact member 105 against the tissue of the human 10. Additionally or alternatively, the controller can also operate the pump 1775 to repeatedly inflate and deflate the inflatable interface 1770 to provide a massage sensation during thermal treatment.

Figure 18A:
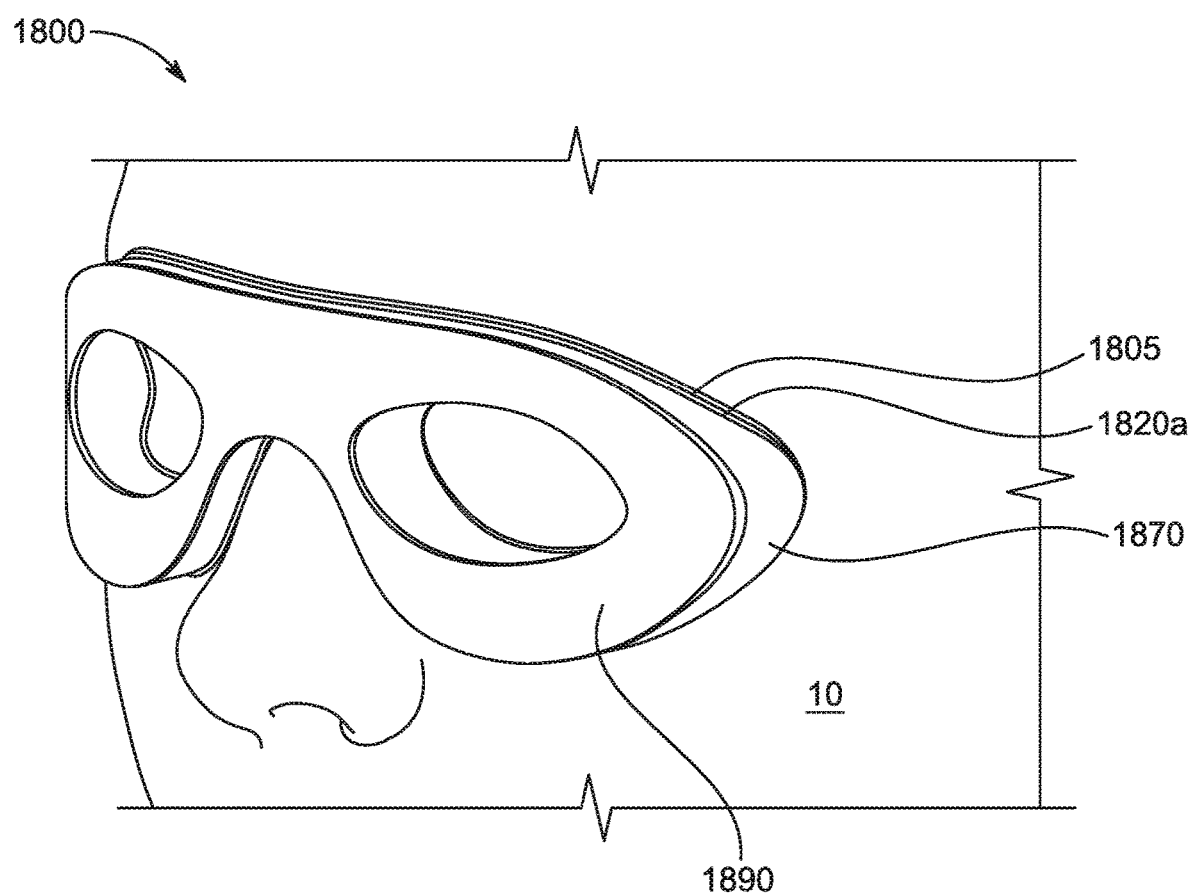
FIG. 18A is a partially schematic isometric view of a heat transfer device being worn by a human, in accordance with embodiments of the present technology.
Figure 18B:
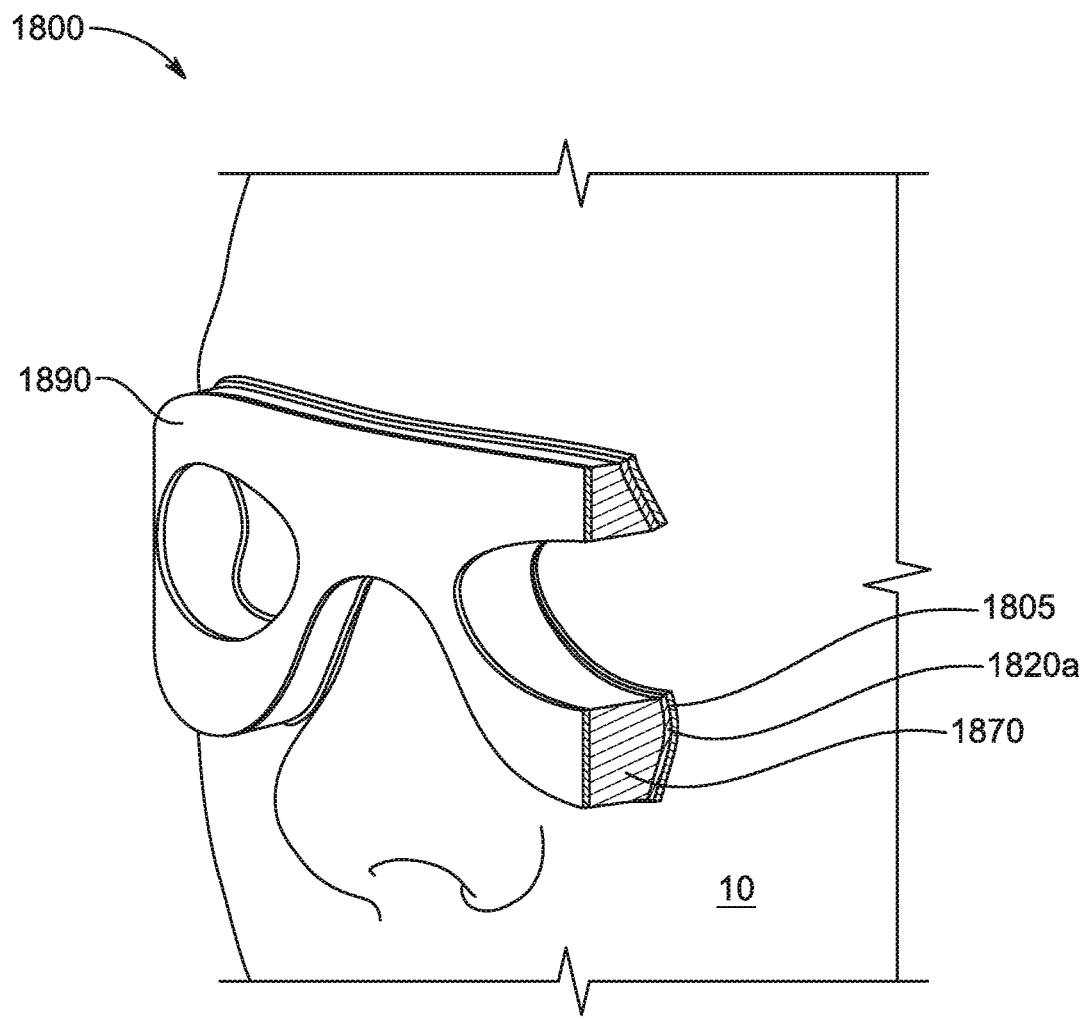
FIG. 18B is partially schematic cross-sectional view of the heat transfer device shown in FIG. 18A.
Figure 18C:
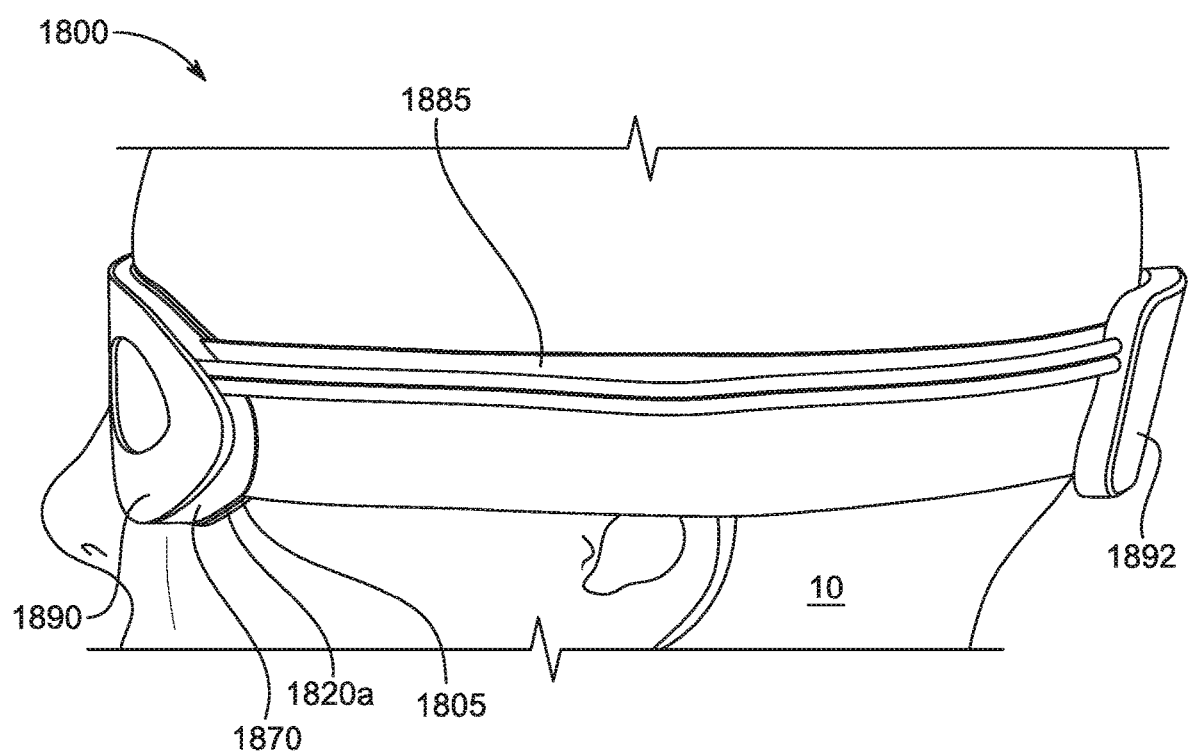
FIG. 18C is a partially schematic side view of the heat transfer device shown in FIGS. 18A and 18B, in accordance with embodiments of the present technology.

FIG. 18A is a partially schematic isometric view of a heat transfer device 1800 ("device 1800") being worn by a human, FIG. 18B is partially schematic isometric cross-sectional view of the device 1800, and FIG. 18C is a partially schematic side view of the device 1800 including an adjustable band 1785. The adjustable band 1785 is omitted from FIGS. 18A and 18B for illustrative purposes. Referring first to FIGS. 18A and 18B, the device 1800 includes a rigid frame 1890 (e.g., the rigid frame 1790 (FIG. 17)), an inflatable interface 1870 (e.g., the inflatable interface 1770 (FIG. 17)) radially inward of the rigid frame 1890, a first heat transfer structure 1820a (e.g., the first heat transfer structure 720a (FIG. 17)) radially inward of the inflatable interface 1870, and a contact member 1805 (e.g., the contact member 105 (FIG. 17)) radially inward of the heat transfer structure 1820a and in contact with the ocular region of the human 10. The contact member 1805 can provide a comfortable contact surface between the device 1800 and the human 10. In some embodiments, the first heat transfer structure 1820a and the contact member 1805 are incorporated into a single element of the device 1800 in contact with the ocular regions of the human 10. As shown in FIG. 18C, the device 1800 can include a rigid member 1892 (e.g., the rigid member 1792 (FIG. 17)) at an opposing side of the human's head relative to the rigid frame 1890, and an adjustable band 1885 (e.g., the adjustable band 1785 (FIG. 17)) extending between the rigid frame 1890 and the rigid member 1892. The rigid member 1892 can comprise and/or contain a second heat transfer structure (e.g., the second heat transfer structure 720b (FIG. 17)), a TEC over and thermally coupled to the second heat transfer structure, a heat exchanger over and thermally coupled to the TEC, and a fan over and thermally coupled to the heat exchanger. The adjustable band can comprise and/or contain a cold fluid passage (e.g., the cold fluid passage 730) extending between the first heat transfer structure and the second heat transfer structure, and a hot fluid passage (e.g., the hot fluid passage 740) extending between the first heat transfer structure and the second heat transfer structure. The adjustable band 1885 can be elastic such that when the device 1800 is worn by the human, the adjustable band 1885 compresses the device 1800 against rigid frame 1890, and therein the contact member 1805, against the ocular region of the human 10.

Figure 19:
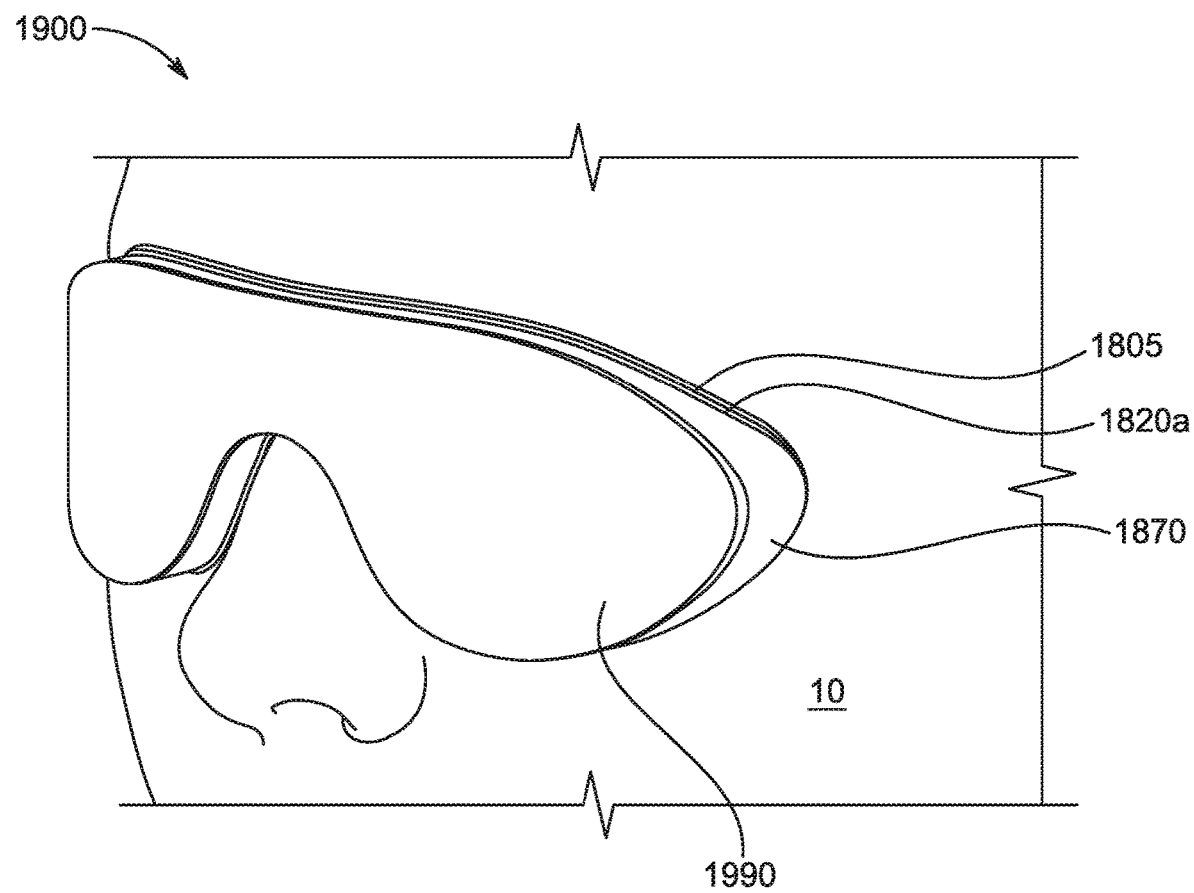
FIG. 19 is a partially schematic isometric view of a heat transfer device being worn by a human, in accordance with embodiments of the present technology.

FIG. 19 is a partially schematic isometric view of a heat transfer device 1900 ("device 1900") being worn by a human 10, in accordance with embodiments of the present technology. The device 1900 is similar to the device 1800 (FIG. 18), but includes a rigid frame 1990 that is fully enclosed and does include openings around the eyes. The device 1900 further includes the inflatable interface 1870 radially inward of the rigid frame 1990 and the contact member 1805 radially inward of the inflatable interface.

Figure 20:
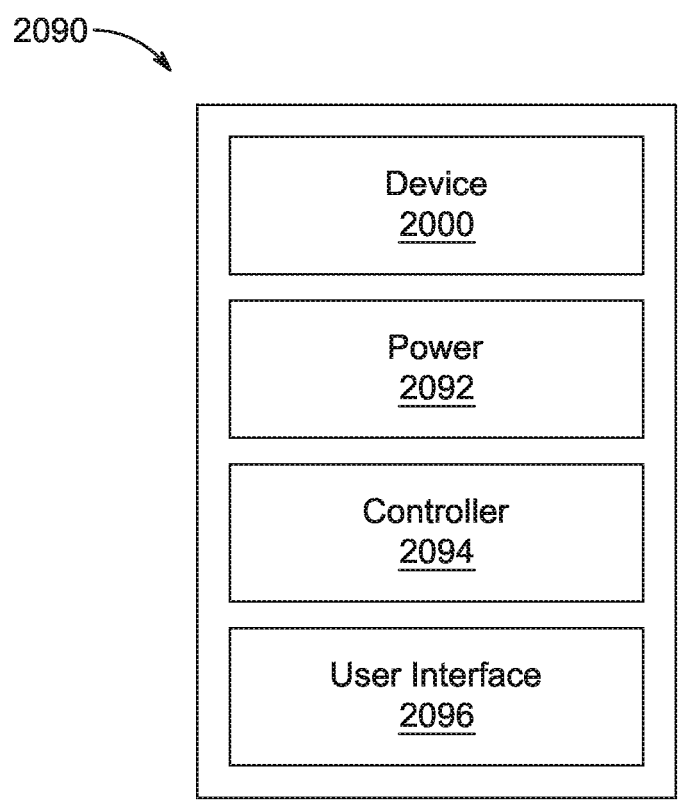
FIG. 20 is a schematic block diagram illustrating a system including a heat transfer device, in accordance with embodiments of the present technology.

FIG. 20 is a schematic block diagram illustrating a system 2090 including a heat transfer device 2000 ("device 2000"), in accordance with embodiments of the present technology. Any one of the heat transfer devices 100, 200, 500, 600, 700, 800, 1000, 1100, 1300, 1400, 1500, 1700, 1800, 1900 described herein with reference to FIGS. 1-19 can be incorporated into a myriad of other and/or more complex systems, a representative example of which is system 2090 shown schematically in FIG. 20. The system 2290 can include the device 2000 (e.g., the heat transfer device 100, 200, 500, 600, 700, 800, 1000, 1100, 1300, 1400, 1500, 1700, 1800, 1900), a power source 2292 (e.g., a portable power source, battery, etc.) operatively coupled to the device 2000 (e.g., to the TECs of the device), a controller 2094 (e.g., a processor) operatively coupled to the device and the power source 2092, a user interface 2096 operatively coupled to the controller 2094 and the power source 2092, as well as other subsystems. The system 2090 can perform any of a wide variety of functions, such as memory storage, data processing, and/or other suitable functions.

The controller 2094 can be configured to operate the device 2000 in one of a plurality of operating modes (e.g., a cooling mode, a heating mode, or both), and/or provide a process value (e.g., a set temperature) at which the device is configured to operate. As previously described with reference to FIG. 1A for example, the controller 2094 can provide a setpoint temperature within a range of 40° C. to −20° C. (e.g., 35° C., 20° C., 0° C., −10° C., etc.) to the device 2000 such that the TECs 110 (e.g., the first or second side of the TECs) are configured to operate at the setpoint temperature. Additionally or alternatively, the controller 2094 can be configured to receive inputs from sensors (e.g., sensor 180 (FIGS. 1A and 1B)) on the device and control the device 2000 based on the received inputs. For example, the controller 2094 can determine any abnormalities of the device 2000 and automatically generate indications of the abnormalities and/or adjust the operating parameters of the device 2000. Additionally or alternatively, the controller 2094 may utilize artificial intelligence and/or machine learning to adjust power and/or other control parameters, e.g., based on previous treatments used for the same human or a group of humans. The user interface 2096 can include a display, and/or an application or program that enables the human to utilize the device through a mobile device (e.g., a phone, tablet, watch, laptop, etc.) or other computing device. The user interface 2096 may include pre-programmed thermal management procedures and/or enable the human to adjust cooling and heating parameters based on a desired application.

Figure 21:
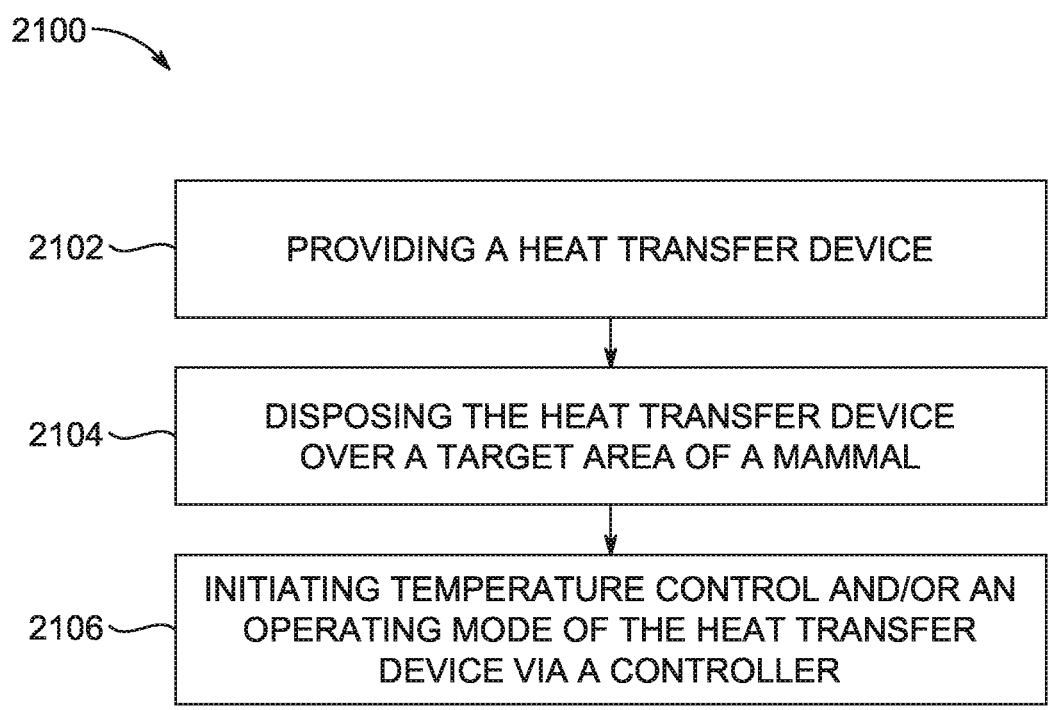
FIG. 21 is a flow diagram illustrating a method for thermally treating a human via a heat transfer device, in accordance with embodiments of the present technology.

FIG. 21 is a flow diagram illustrating a method 2200 for treating a human (e.g., for under eye puffiness, under eye bags, dark circles, or eye hollows) via a heat transfer device, in accordance with embodiments of the present technology. The method 2000 can comprise providing a heat transfer device (e.g., the device 100, 200, 500, 600, 700, 800, 1000, 1100, 1300, 1400, 1500, 1700, 1800, 1900) (process portion 2102), and disposing the heat transfer device over a target area of a human (process portion 2104). Disposing the heat transfer device over the target area can comprise fastening the device over the target area, e.g., such that the device or contact member of the device provides a compressive force on the target area and positions TECs of the device in thermal contact with the target area.

The method 2100 can further comprise initiating temperature control and/or an operating mode of the heat transfer device via a controller (e.g., the controller 2094; FIG. 20), thereby causing heat to transfer from the target area of the human to the heat transfer device or vice versa (process portion 2106). Initiating the operating mode can include initiating a cooling mode, a heating mode, or both a cooling mode and a heating mode. Initiating the temperature control can comprise providing a temperature for the TECs (e.g., the TECs 110; FIGS. 1A, 1B, 2A-14B) to operate at or a temperature at which the device is configured to heat or cool the target area within a predetermined time (e.g., 10 seconds, 20 seconds, 30 seconds, 40 seconds, 60 seconds, or 120 seconds). In some embodiments, the temperature can be set to be within a range of 40° C. to −20° C. (e.g., 35° C., 20° C., 0° C., −10° C., etc.).

V. Conclusion

It will be apparent to those having skill in the art that changes may be made to the details of the above-described embodiments without departing from the underlying principles of the present disclosure. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. The term "and/or" when used in reference to a list of two or more item is to be interpreted as including (a) any single item in the list, (b) all of the items in the list, or (c) any combination of the items in the list. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing numerical values used in the specification and claims, are to be understood as being modified in all instances by the term "about" or "approximately." The terms "about" or "approximately" when used in reference to a value are to be interpreted to mean within 10% of the stated value. Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The present technology is illustrated, for example, according to various aspects described below, as numbered clauses (1, 2, 3, etc.). These clauses are provided as examples and do not limit the present technology. It is noted that any of the dependent clauses may be combined in any combination, and placed into a respective independent clauses. The other clauses can be presented in a similar manner.

1. A heat transfer device, comprising:
   a thermoelectric component (TEC) including a first side configured to be thermally coupled to a target area of a human and a second side opposite the first side;
   a thermally conductive contact member coupled to the first side of the TEC, the contact member being a heat spreader configured to enhance heat transfer to and/or from the target area of the human;
   a heat transfer system configured to distribute heat from the TEC, the heat transfer system including a heat transfer structure thermally coupled to the TEC and a heat exchanger thermally coupled to the heat transfer structure; and
   a rigid frame configured to be worn by the human and including a first region coupled to the contact member and a second region coupled to the heat exchanger, wherein the first region is spaced apart from the second region, and wherein, when the rigid frame is worn by the human, the contact member is adjacent the target area of the human.
2. The device of clause 1, further comprising a cold fluid passage configured to direct a working fluid to the heat transfer structure, and a hot fluid passage configured to direct the working fluid away from the heat transfer structure, wherein the heat transfer structure is spaced apart from the heat exchanger via at least one of the cold fluid passage or the hot fluid passage.
3. The device of clause 2, wherein the cold fluid passage is positioned at a higher elevation than the hot fluid passage.
4. The device of clause 2 or 3, wherein the heat transfer structure is a first heat transfer structure, the device further comprising a second heat transfer structure, wherein the cold fluid passage and the hot fluid passage each extend between the first heat transfer structure and the second heat transfer structure, and wherein the heat exchanger is over the second heat transfer structure such that the heat exchanger in operation removes heat from the second heat transfer structure via at least one of conduction or convection.
5. The device of clause 4, wherein the first heat transfer structure, the second heat transfer structure, the cold fluid passage, and the hot fluid passage comprise a closed-loop system.
6. The device of clause 4 or 5, wherein the heat transfer system is a two-phase system, such that the working fluid directed via the cold fluid passage to the first heat transfer structure comprises a liquid and the working fluid directed via the hot fluid passage from the first heat transfer structure comprises a vapor.
7. The device of clause 4, wherein the TEC is directly over the contact member and the first heat transfer structure is directly over the TEC.
8. The device of clause 4, wherein the TEC is spaced apart from the heat exchanger via at least one of the cold fluid passage or the hot fluid passage.
9. The device of clause 4, wherein the first heat transfer structure is over the contact member, the TEC is over the second heat transfer structure and the heat transfer structure is over the TEC.
10. The device of clause 4, wherein the TEC is spaced apart from the contact member via at least one of the cold fluid passage or the hot fluid passage.
11. The device of any one of the clauses herein, wherein the heat transfer structure comprises an inlet region, an outlet region, and microfeatures spaced apart from each other to at least partially define channels configured to receive a working fluid, wherein, in operation, the working fluid flows from the inlet region to the outlet region and absorbs heat from the microfeatures.

12. The device of clause 1, wherein:
the contact member is coupled to the TEC and configured such that, when the contact member is attached to the human, the TEC is arranged to be adjacent the target area, and
the heat transfer structure comprises a heat pipe extending from the TEC to the heat exchanger.

13. The device of clause 12, wherein the heat pipe includes an evaporator portion adjacent the TEC and a condenser portion adjacent the heat exchanger, and wherein the heat pipe includes an outer metal material, a wicking material radially inward of the outer metal material, and a void radially inward of the outer metal material.

14. The device of clause 13, further comprising a heat spreader coupled to the heat exchanger and the condenser portion of the heat pipe.

15. The device of any one of the clauses herein, wherein the first region of the rigid frame comprises one of a bridge portion or end portion of the rigid frame, and the second region of the rigid frame comprises a temple portion of the rigid frame.

16. A wearable heat transfer device configured to provide thermal treatment to an ocular region of a human, the device comprising:
thermoelectric components (TECs) arranged in an array and spaced apart from one another, wherein individual TECs include a first side configured to be thermally coupled to a target ocular region of a human and a second side opposite the first side;
a thermally conductive contact member coupled to the first sides of the TECs and positioned to transfer heat to and/or from the target ocular region of the human;
a heat transfer system configured to distribute heat from the TEC, the heat transfer system including a heat transfer structure thermally coupled to the TEC, and a heat exchanger thermally coupled to the heat transfer structure, wherein the contact member is spaced apart from the heat exchanger; and
a controller coupled to the TEC, wherein the controller is configured to operate the TEC and the heat transfer system such that the heat transfer system cools the second side of the TEC to a first temperature and the TEC causes the temperature of the target ocular region to change to a second temperature, different than the first temperature, within a predetermined period of time.

17. The device of clause 16, further comprising a cold fluid passage configured to direct a working fluid to the heat transfer structure, and a hot fluid passage configured to direct the working fluid away from the heat transfer structure, wherein the heat transfer structure is spaced apart from the heat exchanger via at least one of the cold fluid passage or the hot fluid passage.

18. The device of clause 17, wherein the cold fluid passage is positioned at a higher elevation than the hot fluid passage.

19. The device of clause 17 or 18, wherein the heat transfer structure is a first heat transfer structure, the device further comprising a second heat transfer structure, wherein the cold fluid passage and the hot fluid passage each extend between the first heat transfer structure and the second heat transfer structure, and wherein the heat exchanger is over the second heat transfer structure such that the heat exchanger in operation removes heat from the second heat transfer structure via at least one of conduction or convection.

20. The device of clause 16, wherein the first side of the individual TECs is coupled to the contact member such that the individual TECs are thermally coupled to the target ocular region via the contact member, and wherein the second side of the individual TECs is coupled to the heat transfer structure.

21. The device of clause 16, wherein the heat transfer structure is over the contact member and thermally coupled to the first side of the individual TECs, and wherein the individual TECs are coupled to the heat exchanger such that the heat exchanger is configured to cool the second side of the individual TECs.

22. The device of clause 16, wherein the heat transfer structure comprises an elongate heat pipe including an evaporation portion thermally coupled to the second side of the TEC and a condenser portion thermally coupled to the heat exchanger.

23. The device of clause 22, wherein the heat pipe includes an outer metal material, a wicking material radially inward of the outer metal material, and a void radially inward of the outer metal material, the void containing a working fluid that, during operation of the device, transitions from a vapor at the evaporation portion to a liquid at the condenser portion.

24. The device of any one of the clauses herein, further comprising a rigid frame configured to be worn by the human and including edge portions, a bridge portion extending between the edge portions in a first direction, and a temple portion extending from the edge portions in a second direction different than the first direction, wherein the contact member is coupled to at least one of the bridge portion or the end portions and the heat exchanger is coupled to the temple portion.

25. A heat transfer device, comprising:
a thermoelectric component (TEC) including a first side configured to be operated at a desired temperature and a second side opposite the first side;
a contact member thermally coupled to the TEC, the contact member comprising a thermally conductive material and being configured to enhance heat transfer to and/or from a target area of a human;
a heat transfer system configured to distribute heat from the TEC, the heat transfer system including a heat transfer structure thermally coupled to the TEC, and a heat exchanger thermally coupled to the heat transfer structure; and
an inflatable interface over and radially outward from the contact member, wherein the inflatable interface, when inflated, applies pressure toward contact member.

26. The device of clause 25, further comprising a rigid frame radially outward of the inflatable interface and configured to be over a first side of the human; and an adjustable band extending from the rigid frame and configured to be worn around a second side, opposite the first side, of the human, wherein, when worn by the human, the adjustable strap causes the rigid frame to exert pressure against the first side of the human.

27. The device of clause 26, wherein the heat transfer structure is disposed between the contact member and the inflatable interface, the heat transfer system further comprising (i) a cold fluid passage fluidically coupled to an inlet region of the heat transfer structure and configured to provide a cooled working fluid to the heat transfer structure, and (ii) a hot fluid passage fluidically coupled to an outlet region of the heat transfer structure and configured to receive a heated working fluid from the heat transfer structure, wherein the cold fluid passage and the hot fluid passage extend along at least a portion of the adjustable strap.

28. The device of clause 27, wherein the heat transfer structure is a first heat transfer structure, the device further comprising a second heat transfer structure thermally coupled to the first side of the TEC and fluidically coupled to the cold fluid passage and the hot fluid passage, wherein the second heat transfer structure is configured to provide the cooled working fluid to the cold fluid passage and receive the heated working fluid from the hot fluid passage.

29. The device of clause 25, wherein the TEC is coupled to the heat exchanger such that the second side of the TEC is configured to be cooled by the heat exchanger, and wherein the TEC and the heat exchanger are spaced apart from the contact member.

30. The device of clause 25, further comprising a controller, and a pump operably coupled to the controller and fluidically coupled to the inflatable interface, wherein the pump is configured to inflate and/or deflate the inflatable interface based on a signal received from the controller.

We claim:

1. A heat transfer device, comprising:
  a thermoelectric component (TEC) including a first side configured to be thermally coupled to a target area of a human and a second side opposite the first side;
  a thermally conductive contact member coupled to the first side of the TEC, the contact member being a heat spreader configured to enhance heat transfer to and/or from the target area of the human;
  a heat transfer system configured to distribute heat from the TEC, the heat transfer system including a heat transfer structure thermally coupled to the TEC and a heat exchanger thermally coupled to the heat transfer structure; and
  a rigid frame sized and shaped to be worn around and supported by a facial region of the human and including (i) a first region coupled to the contact member and (ii) a second region mounted to the heat exchanger and having a length, wherein the second region extends from the first region and includes a rigid material extending along an entirety of the length of the second region, and wherein, when the rigid frame is worn by the human, the contact member is adjacent the target area of the human.

2. The device of claim 1, further comprising a cold fluid passage configured to direct a working fluid to the heat transfer structure, and a hot fluid passage configured to direct the working fluid away from the heat transfer structure, wherein the heat transfer structure is spaced apart from the heat exchanger via at least one of the cold fluid passage or the hot fluid passage.

3. The device of claim 2, wherein an entirety of the cold fluid passage is positioned at a higher elevation than an entirety of the hot fluid passage.

4. The device of claim 2, wherein the heat transfer structure is a first heat transfer structure, the device further comprising a second heat transfer structure, wherein the cold fluid passage and the hot fluid passage each extend between the first heat transfer structure and the second heat transfer structure, and wherein the heat exchanger is over the second heat transfer structure such that the heat exchanger in operation removes heat from the second heat transfer structure via at least one of conduction or convection.

5. The device of claim 4, wherein the first heat transfer structure, the second heat transfer structure, the cold fluid passage, and the hot fluid passage comprise a closed-loop system.

6. The device of claim 4, wherein the heat transfer system is a two-phase system, such that the working fluid directed via the cold fluid passage to the first heat transfer structure comprises a liquid and the working fluid directed via the hot fluid passage from the first heat transfer structure comprises a vapor.

7. The device of claim 4, wherein the TEC is directly over the contact member and the first heat transfer structure is directly over the TEC.

8. The device of claim 4, wherein the TEC is spaced apart from the heat exchanger via at least one of the cold fluid passage or the hot fluid passage.

9. The device of claim 4, wherein the first heat transfer structure is over the contact member, and wherein the TEC is over the first heat transfer structure and the second heat transfer structure is over the TEC.

10. The device of claim 4, wherein the TEC is spaced apart from the contact member via at least one of the cold fluid passage or the hot fluid passage.

11. The device of claim 1, wherein the heat transfer structure comprises an inlet region, an outlet region, and microfeatures spaced apart from each other to at least partially define channels configured to receive a working fluid, wherein, in operation, the working fluid flows from the inlet region to the outlet region and absorbs heat from the microfeatures.

12. The device of claim 1, wherein:
  the contact member is coupled to the TEC and configured such that, when the contact member is attached to the human, the TEC is arranged to be adjacent the target area, and
  the heat transfer structure comprises a heat pipe extending from the TEC to the heat exchanger.

13. The device of claim 12, wherein the heat pipe includes an evaporator portion adjacent the TEC and a condenser portion adjacent the heat exchanger, and wherein the heat pipe includes an outer metal material, a wicking material radially inward of the outer metal material, and a void radially inward of the outer metal material.

14. The device of claim 13, further comprising a heat spreader coupled to the heat exchanger and the condenser portion of the heat pipe.

15. The device of claim 1, wherein the first region of the rigid frame comprises one of a bridge portion or end portion of the rigid frame, and the second region of the rigid frame comprises a temple portion of the rigid frame.

16. A wearable heat transfer device sized and shaped to be worn around a facial region of a human and configured to provide thermal treatment to an ocular region of the human, the device comprising:
  thermoelectric components (TECs) arranged in an array and spaced apart from one another, wherein individual TECs include a first side configured to be thermally coupled to a target ocular region of a human and a second side opposite the first side;
  a thermally conductive contact member coupled to the first sides of the TECs and positioned to transfer heat to and/or from the target ocular region of the human;
  a heat transfer system configured to distribute heat from the TECs, the heat transfer system including (i) a heat transfer structure thermally coupled to the TECs and (ii) a heat exchanger thermally coupled to the heat transfer structure, wherein the contact member is spaced apart from the heat exchanger;
a rigid frame including (i) a first region coupled to the contact member and (ii) a second region mounted to the heat exchanger and having a length, wherein the second region extends from the first region and includes a rigid material extending along an entirety of the length of the second region; and
a controller coupled to the TECs, wherein the controller is configured to operate the TECs and the heat transfer system such that the heat transfer system cools the second sides of the TECs to a first temperature and the TECs cause the temperature of the target ocular region to change to a second temperature, different than the first temperature, within a predetermined period of time.

17. The device of claim 16, further comprising a cold fluid passage configured to direct a working fluid to the heat transfer structure, and a hot fluid passage configured to direct the working fluid away from the heat transfer structure, wherein the heat transfer structure is spaced apart from the heat exchanger via at least one of the cold fluid passage or the hot fluid passage.

18. The device of claim 17, wherein the cold fluid passage is positioned at a higher elevation than the hot fluid passage.

19. The device of claim 17, wherein the heat transfer structure is a first heat transfer structure, the device further comprising a second heat transfer structure, wherein the cold fluid passage and the hot fluid passage each extend between the first heat transfer structure and the second heat transfer structure, and wherein the heat exchanger is over the second heat transfer structure such that the heat exchanger in operation removes heat from the second heat transfer structure via at least one of conduction or convection.

20. The device of claim 16, wherein the first side of the individual TECs is coupled to the contact member such that the individual TECs are thermally coupled to the target ocular region via the contact member, and wherein the second side of the individual TECs is coupled to the heat transfer structure.

21. The device of claim 16, wherein the heat transfer structure is over the contact member and thermally coupled to the first side of the individual TECs, and wherein the individual TECs are coupled to the heat exchanger such that the heat exchanger is configured to cool the second side of the individual TECs.

22. The device of claim 16, wherein the heat transfer structure comprises an elongate heat pipe including an evaporation portion thermally coupled to the second sides of the TECs and a condenser portion thermally coupled to the heat exchanger.

23. The device of claim 22, wherein the heat pipe includes an outer metal material, a wicking material radially inward of the outer metal material, and a void radially inward of the outer metal material, the void containing a working fluid that, during operation of the device, transitions from a vapor at the evaporation portion to a liquid at the condenser portion.

24. The device of claim 16, wherein the rigid frame is configured to be worn by the human and the first region of the rigid frame comprises edge portions and a bridge portion extending between the edge portions in a first direction, and the second region of the rigid frame comprises a temple portion extending from the edge portions in a second direction different than the first direction, wherein the contact member is coupled to at least one of the bridge portion or the edge portions and the heat exchanger is mounted to the temple portion.

25. A heat transfer device, comprising:
a thermoelectric component (TEC) including a first side configured to be operated at a desired temperature and a second side opposite the first side;
a contact member thermally coupled to the TEC, the contact member comprising a thermally conductive material and being configured to enhance heat transfer to and/or from a target area of a human;
a heat transfer system configured to distribute heat from the TEC, the heat transfer system including a heat transfer structure thermally coupled to the TEC, and a heat exchanger thermally coupled to the heat transfer structure; and
an inflatable interface over and radially outward from the contact member,
wherein the inflatable interface, when inflated, applies pressure toward the contact member, and
wherein the heat transfer device is sized and shaped to be worn around a facial region of a human and includes (i) a rigid frame coupled to the inflatable interface and (ii) a rigid member mounted to the heat exchanger.

26. The device of claim 25, further comprising:
the rigid frame outward of the inflatable interface and configured to be over a first side of the facial region of the human;
the rigid member configured to be to be worn around a second side, opposite the first side, of the facial region of the human; and
an adjustable band extending from the rigid frame to the rigid member,
wherein, when worn by the human, the adjustable band causes the rigid frame to exert pressure against the first side.

27. The device of claim 26, wherein the heat transfer structure is disposed between the contact member and the inflatable interface, the heat transfer system further comprising (i) a cold fluid passage fluidically coupled to an inlet region of the heat transfer structure and configured to provide a cooled working fluid to the heat transfer structure, and (ii) a hot fluid passage fluidically coupled to an outlet region of the heat transfer structure and configured to receive a heated working fluid from the heat transfer structure, wherein the cold fluid passage and the hot fluid passage extend along at least a portion of the adjustable strap.

28. The device of claim 27, wherein the heat transfer structure is a first heat transfer structure, the device further comprising a second heat transfer structure thermally coupled to the first side of the TEC and fluidically coupled to the cold fluid passage and the hot fluid passage, wherein the second heat transfer structure is configured to provide the cooled working fluid to the cold fluid passage and receive the heated working fluid from the hot fluid passage.

29. The device of claim 25, wherein the TEC is coupled to the heat exchanger such that the second side of the TEC is configured to be cooled by the heat exchanger, and wherein the TEC and the heat exchanger are spaced apart from the contact member.

30. The device of claim 25, further comprising:
a controller; and
a pump operably coupled to the controller and fluidically coupled to the inflatable interface, wherein the pump is configured to inflate and/or deflate the inflatable interface based on a signal received from the controller.

* * * * *

UNITED STATES PATENT AND TRADEMARK OFFICE
CERTIFICATE OF CORRECTION

PATENT NO. : 12,059,371 B2
APPLICATION NO. : 18/149574
DATED : August 13, 2024
INVENTOR(S) : Sahar Jahani et al.

It is certified that error appears in the above-identified patent and that said Letters Patent is hereby corrected as shown below:

In the Specification

In Column 3, Line 19, delete "Eye" and insert -- eye --.

In Column 8, Line 39, delete "structure120" and insert -- structure 120 --.

In Column 19, Line 3, delete "strap1305" and insert -- strap 1305 --.

In Column 19, Line 50, delete "strap1305" and insert -- strap 1305 --.

In Column 19, Line 52, delete "strap1305," and insert -- strap 1305, --.

Signed and Sealed this
Twenty-ninth Day of April, 2025

Coke Morgan Stewart
*Acting Director of the United States Patent and Trademark Office*